(12) United States Patent
Han et al.

(10) Patent No.: US 11,840,739 B2
(45) Date of Patent: Dec. 12, 2023

(54) GENE COMPOSITION FOR DETECTING CELL PROLIFERATIVE ABNORMALITY OR GRADING DISEASE DEGREE AND USE THEREOF

(71) Applicant: Biochain (Beijing) Science & Technology, Inc., Beijing (CN)

(72) Inventors: Xiaoliang Han, Newark, CA (US); Tong Lu, Newark, CA (US); Kaichun Wu, Shaanxi Province (CN); Yongzhan Nie, Shaanxi Province (CN); Daiming Fan, Shaanxi Province (CN); James Jianming Wang, Newark, CA (US)

(73) Assignee: Biochain(Beijing) Science & Technology, Inc., Beijing (CN)

( * ) Notice: Subject to any disclaimer, the term of this patent is extended or adjusted under 35 U.S.C. 154(b) by 19 days.

(21) Appl. No.: 17/221,274

(22) Filed: Apr. 2, 2021

(65) Prior Publication Data
US 2021/0292847 A1    Sep. 23, 2021

Related U.S. Application Data

(62) Division of application No. 15/500,771, filed as application No. PCT/CN2015/086367 on Aug. 7, 2015, now Pat. No. 10,968,486.

(30) Foreign Application Priority Data

Aug. 8, 2014 (CN) .......................... 201410389895.2

(51) Int. Cl.
    *C12Q 1/6886*    (2018.01)
    *C12Q 1/6813*    (2018.01)
    *C12N 15/11*     (2006.01)

(52) U.S. Cl.
    CPC ............ *C12Q 1/6886* (2013.01); *C12N 15/11* (2013.01); *C12Q 1/6813* (2013.01); *C12Q 2600/154* (2013.01)

(58) Field of Classification Search
    None
    See application file for complete search history.

(56) References Cited

U.S. PATENT DOCUMENTS 5,541,308 A    7/1996  Hogan et al.
7,749,702 B2   7/2010  Loften-Day et al.
2008/0213791 A1  9/2008  Freije et al.
2011/0151443 A1  6/2011  Sung et al.
2013/0129668 A1  5/2013  Firestein et al.

FOREIGN PATENT DOCUMENTS

| CN | 101160411 | 4/2008 |
| CN | 103732759 | 4/2014 |
| CN | 103789428 | 5/2014 |
| CN | 104745575 | 7/2015 |
| WO | WO-2007/102891 A1 | 9/2007 |

OTHER PUBLICATIONS

Cheung (Cancer, 2012, 118:947-59).*
Cottrell (Clin. Biochem. 37(2004) 595-604).*
Feinberg (Nature Reviews, 2004, vol. 4, pp. 143-153).*
Smiraglia et al. (Human Molecular Genetics 2001 vol. 10, pp. 1413-1419).*
Verma et al. (Critical Review in Oncology/Hematology 60 (2006), pp. 9-18).*
Jones et al. (Nature Reviews, 2002, vol. 3, pp. 415-428).*
Buck et al "Design Strategies and Performance of Custom DNA Sequencing Primers" BioTechniques vol. 27, pp. 528-536, 1999.
Deng et al "Methylation of CpG Sites in RNF180 DNA Promoter Prediction Poor Survival of Gastric Cancer" Oncotarget vol. 5, pp. 3173-3183, 2014.
Lee et al "Circulating Methylated Septin 9 Nucleic Acid in the Plasma of Patients with Gastrointestinal Cancer in the Stomach and Colon" Translational Oncology vol. 6, pp. 290-296, 2013.
Li et al "Epigenetic Biomarkers: Potential Applications in Gastrointestinal Cancers" ISRN Gastroenterology vol. 2014, pp. 1-10, 2014.
Li et al "MethPrimer: Designing Primers for Methylation PCRs" Bioinformatics vol. 18, pp. 1427-1431, 2002.
Zhang et al "Detection of Aberrant Promoter Methylation of RNF180, DAPK1, and SFRP2 in Plasma DNA of Patients with Gastric Cancer" Oncology Letters vol. 8, pp. 1745-1750, 2014.
Zhang et al "Septin 9 Gene Methylation in Gastric Carcinoma and its Clinical Significance" Chinese Journal of Health Laboratory Technology vol. 24, pp. 1987-1990, 2014, Abstract only, not in English.

* cited by examiner

*Primary Examiner* — Sarae L Bausch
(74) *Attorney, Agent, or Firm* — Morse, Barnes-Brown & Pendleton, P.C.; Martin Z. Zhang; Russell L. Widom

(57) ABSTRACT

The present invention provides a composition, a kit and the use thereof, as well as the method for detecting the cell proliferative abnormality in individuals or grading the disease degree in the individuals. The composition comprises nucleic acids for detecting the methylation level within at least one target region of a gene and the fragment thereof.

4 Claims, 11 Drawing Sheets

Specification includes a Sequence Listing.

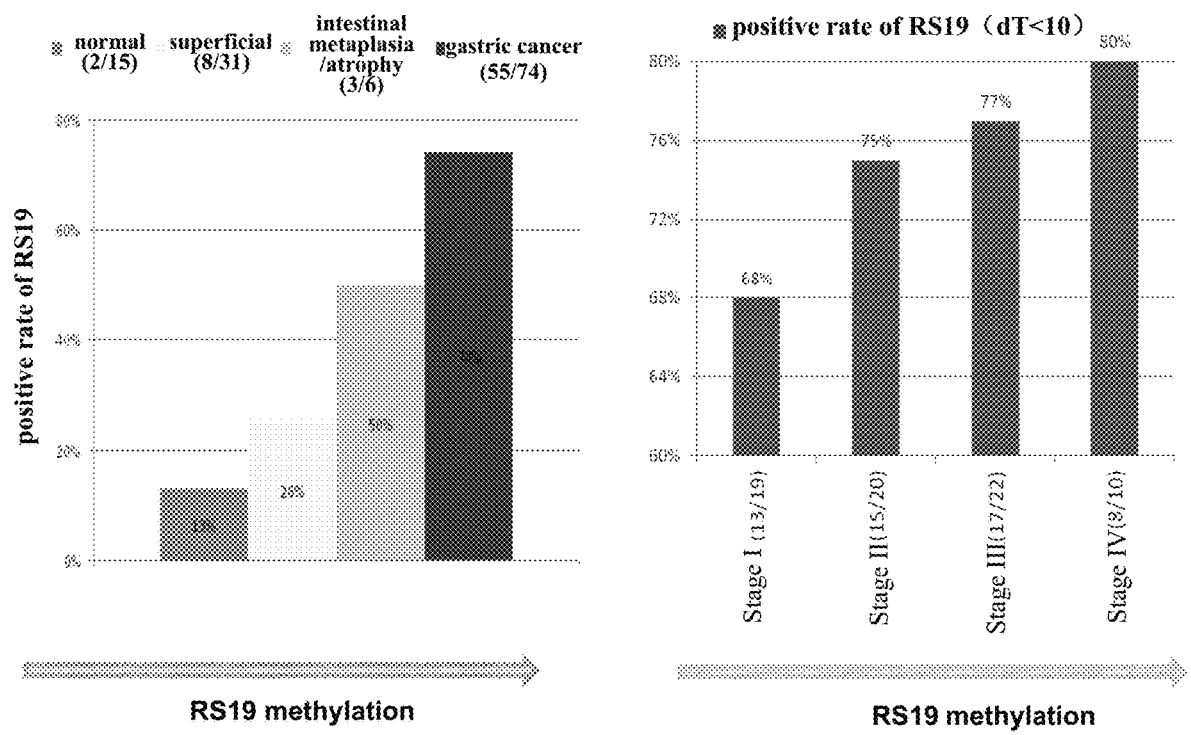
Figure 7A
Figure 7B
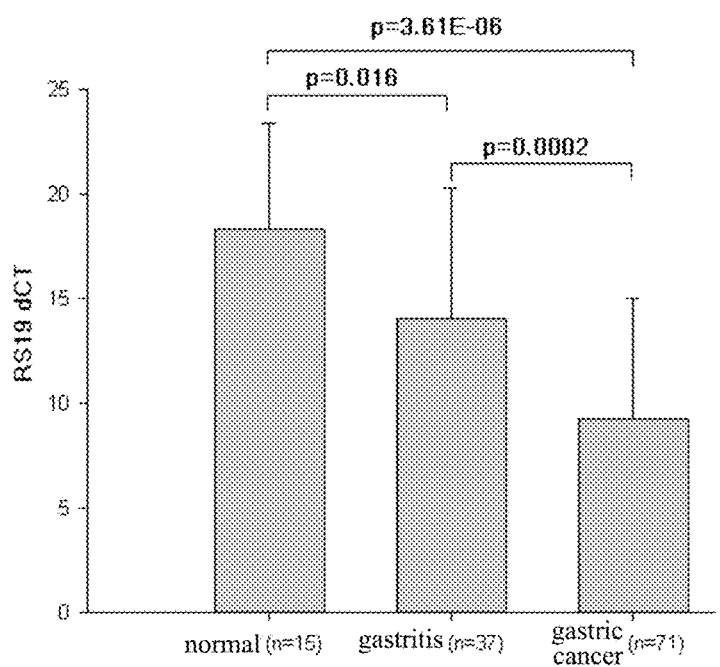
Figure 7C

GENE COMPOSITION FOR DETECTING CELL PROLIFERATIVE ABNORMALITY OR GRADING DISEASE DEGREE AND USE THEREOF

CROSS-REFERENCE TO RELATED APPLICATIONS

The present application is a divisional of U.S. patent application Ser. No. 15/500,771, filed on Jul. 5, 2017, now U.S. Pat. No. 10,968,486, which is the National Stage of International Application No. PCT/CN2015/086367, filed on Aug. 7, 2015, which claims the benefit of Chinese Application No. 2014103898952, filed on Aug. 8, 2014. The contents of all prior applications are hereby incorporated by reference in their entirety.

TECHNICAL FIELD

The present invention relates to gene detection, particularly relates to a gene composition and use of the gene composition for detecting abnormal cell proliferation in an individual or grading disease severity.

BACKGROUND ART

The disease caused by abnormal cell proliferation, such as cancer, is a major challenge for public health. In the United States, the death toll due to cancers accounts for about 25% of the total death toll. Among these, gastric cancer, as the fourth cancer most commonly diagnosed in the world with the second mortality ranking in all cancers, is considered as one of the largest enemies to health worldwide. Especially in many Asian countries including in China, gastric cancer ranks first in various malignancies, with very high morbidity and mortality.

Gastritis is a general name for the inflammation in gastric mucosa, which is common in adults. Many etiological factors, such as improper diets, viral and bacterial infections, drug stimulation, can stimulate stomach and cause gastritis, but gastritis is relatively easy to be corrected and treated.

However, it is often easy to confuse the symptoms of gastritis and gastric cancer, so that many people often mistake gastritis for gastric cancer in daily life and fear all day long. Even if gastritis is not a serious disease, it will continue to deteriorate due to psychological effects. Meanwhile, some people mistake gastric cancer for gastritis and overlook it, and believe that it is not a serious problem. As a result, they miss the best time for treatment.

Therefore, there is an urgent need for a detection method with high sensitivity and specificity so as to distinguish among normal, gastritis and gastric cancer, in particular for a detection method with high sensitivity and specificity without pain.

With the continuous development of biotechnology, use of gene detection in diagnosis method for diseases has attracted extensive attentions. Among these, DNA methylation is an important component of epigenetics, which plays an important role not only in the maintenance of normal cell functions, but also in the occurrence of cancer and inflammation, that is, the change of methylation status is an important factor in the occurrence of cancer and inflammation, and includes decreased methylation level of whole genome and abnormally increased local methylation level of CpG island, leading to instable genome and expression failure of disease-resistant genes. If an active allele of a disease-resistant gene is inactivated, the risk of the occurrence of cancer and inflammation will increase. Therefore, a reasearch on methylation provides a new basis for the early prediction, classification, grading and prognosis evaluation of cancer and inflammation, and becomes one of the current research focuses.

CONTENTS OF INVENTION

Therefore, the present invention provides a gene composition and a kit for detecting abnormal cell proliferation in an individual or grading disease severity (such as gastric cancer and gastritis) by detecting the methylation level, and use thereof, as well as a method for performing the detection based on the kit.

Accordingly, according to the first aspect of the present invention, provided is a composition comprising a nucleic acid for detecting the methylation level within at least one target region of RNF180 and Septin9 genes, or fragments thereof.

Typically, the nucleic acid comprises a long fragment of at least 15 oligonucleotides of RNF180, wherein the oligonucleotides comprise at least one CpG dinucleotide sequence.

According to the certain preferred embodiments, the long nucleotide fragment of RNF180 comprises at least 15 nucleotides which are equivalent to, complementary to, or hybridize under moderately stringent or stringent conditions to a sequence selected from the group consisting of SEQ ID Nos: 10 to 12, or complementary sequence thereof.

Further preferably, the long nucleotide fragment of RNF180 comprises a sequence which is equivalent to, complementary to, or hybridizes under moderately stringent or stringent conditions to a sequence selected from the group consisting of SEQ ID Nos: 1 to 9, or complementary sequence thereof.

Typically, the composition further comprises a reagent that converts 5-unmethylated cytosine base of a gene to uracil or other base that is detectably different from cytosine in terms of hybridization performance. Preferably, the reagent is bisulfite.

According to the second aspect of the present invention, further provided is a kit comprising the composition described above.

Typically, the kit comprises a container for containing a biological sample from a patient.

Also, the kit may also comprise the instructions for using the kit and explaining the results of the kit.

According to the third aspect of the present invention, further provided is use of the composition in the manufacture of a kit for detecting abnormal cell proliferation in an individual.

Typically, the abnormal cell proliferation is a cancer. Preferably, the cancer is gastric cancer.

According to the fourth aspect of the present invention, further provided is a method for detecting abnormal cell proliferation in an individual, comprising determining the methylation level within at least one target region of RNF180 and Septin9 genes or fragments thereof in a biological sample isolated from the individual, and detecting abnormal cell proliferation in the individual by combining the detection results of methylation of RNF180 and Septin9.

Typically, the method further comprises: treating Septin9 and RNF180 genes or fragments thereof with a reagent which convert 5-unmethylated cytosine base of a gene to uracil or other base that is detectably different from cytosine in terms of hybridization performance; contacting Septin9 and RNF180 genes or fragments thereof treated by the reagent with an amplification enzyme and primers such that the treated genes or fragments are amplified to produce amplification products or not amplified; detecting the amplification products with probes; and determining the methylation level of at least one CpG dinucleotide of the DNA sequences of Septin9 and RNF180 genes based on the presence or absence of the amplification products.

Typically, the primers comprise a long nucleotide fragment of RNF180 comprising at least 15 nucleotides which are equivalent to, complementary to, or hybridize under moderately stringent or stringent conditions to a sequence selected from the group consisting of SEQ ID Nos: 10 to 12, or complementary sequence thereof.

Preferably, the long nucleotide fragment of RNF180 comprises a sequence which is equivalent to, complementary to, or hybridizes under moderately stringent or stringent conditions to a sequence selected from the group consisting of SEQ ID Nos: 1 to 9, and complementary sequence thereof.

Wherein, the primers and probes are preferably screened with an artificially methylated template and an unmethylated template; or the primers and probes are screened with cancer and normal DNA as templates.

Typically, the biological sample of an individual is selected from the group consisting of cell lines, histological sections, tissue biopsies/paraffin-embedded tissues, body fluids, stool, colonic effluent, urine, plasma, serum, whole blood, isolated blood cells, cells isolated from blood, or combination thereof.

Preferably, the biological sample of an individual is plasma.

According to certain preferred embodiments, the methylation status of at least one CpG dinucleotide of the DNA sequences of Septin9 and RNF180 gene is determined by the cycle threshold Ct value of a polymerase chain reaction.

Typically, the abnormal cell proliferation is a cancer. Preferably, the cancer is gastric cancer.

Accordingly, according to another aspect of the present invention, provided is use of a composition in the manufacture of a kit for grading disease severity in an individual. The composition comprises a nucleic acid for detecting the methylation level within at least one target region of RNF180 gene or fragment thereof, and the disease severity is graded by the detection result of the methylation level of RNF180.

According to certain preferred embodiments of the present invention, the composition further comprises a nucleic acid for detecting the methylation level within at least one target region of Septin9 gene or fragment thereof, and the disease severity is graded by combining the detection results of methylation of RNF180 and Septin9.

Typically, the nucleic acid comprises a long fragment of at least 15 oligonucleotides of RNF180, wherein the oligonucleotides comprise at least one CpG dinucleotide sequence.

Preferably, the nucleotide long fragment of RNF180 comprises at least 15 nucleotides which are equivalent to, complementary to, or hybridize under moderately stringent or stringent conditions to a sequence selected from the group consisting of SEQ ID Nos: 10 to 12, or complementary sequence thereof.

Further preferably, the nucleotide long fragment of RNF180 comprises a sequence which is equivalent to, complementary to, or hybridizes under moderately stringent or stringent conditions to a sequence selected from the group consisting of SEQ ID Nos: 1 to 9, or complementary sequence thereof.

Typically, the composition further comprises a reagent that converts 5-unmethylated cytosine base of a gene to uracil or other base that is detectably different from cytosine in terms of hybridization performance. Preferably, the reagent is bisulfite.

Typically, the disease severity is divided into three levels, and the first level is normal, the second level is inflammation and the third level is cancer. In certain preferred embodiments, the inflammation is gastritis, and the cancer is gastric cancer. Preferably, the gastritis can be further graded into the gastritis that is less prone to canceration and the gastritis that is prone to canceration. The gastritis that is less prone to canceration is superficial gastritis. Further preferably, the gastritis that is prone to canceration is further graded into atrophic gastritis and gastritis with intestinal metaplasia. Further preferably, gastric cancer may be further graded into gastric cancer stages I, II, III and IV.

According to another aspect of the present invention, provided is a method for grading disease severity in an individual, comprising determining the methylation level within at least one target region of RNF180 or fragment thereof in a biological sample isolated from the individual, and grading the disease severity by the detection result of methylation of RNF180.

Typically, the method further comprises determining the methylation level within at least one target region of Septin9 gene or fragment thereof in a biological sample isolated from the individual, and grading the disease severity by combining the detection results of methylation of RNF180 and Septin9.

According to certain preferred embodiments, the method further comprises: treating Septin9 and RNF180 genes or fragments thereof with a reagent which converts 5-unmethylated cytosine base of a gene to uracil or other base that is detectably different from cytosine in terms of hybridization performance; contacting Septin9 and RNF180 genes or fragments thereof treated by the reagent with an amplification enzyme and primers such that the treated genes or fragments are amplified to produce amplification products or not amplified; detecting the amplification products with probes; and determining the methylation level of at least one CpG dinucleotide of the DNA sequences of Septin9 and RNF180 gene based on the presence or absence of the amplification products.

Typically, the primers comprises a nucleotide long fragment of RNF180 comprising at least 15 nucleotides which are equivalent to, complementary to, or hybridize under moderately stringent or stringent conditions to a sequence selected from the group consisting of SEQ ID Nos: 10 to 12, or complementary sequence thereof.

Preferably, the nucleotide long fragment of RNF180 comprises a sequence which is equivalent to, complementary to, or hybridizes under moderately stringent or stringent conditions to a sequence selected from the group consisting of SEQ ID Nos: 1 to 9, or complementary sequence thereof.

Wherein, the primers and probes are preferably screened with an artificially methylated template and an unmethylated template; or the primer and probes are screened with cancer and normal DNA as templates.

Typically, the biological sample of an individual is selected from the group consisting of cell lines, histological sections, tissue biopsies/paraffin-embedded tissues, body fluids, stool, colonic effluent, urine, plasma, serum, whole blood, isolated blood cells, cells isolated from blood, or combination thereof.

Preferably, the biological sample of an individual is plasma.

According to certain preferred embodiments, the methylation status of at least one CpG dinucleotide of the DNA sequences of Septin9 and RNF180 genes is determined by the cycle threshold Ct value of a polymerase chain reaction.

Typically, the disease severity is divided into three levels, and the first level is normal, the second level is inflammation and the third level is cancer.

According to another aspect of the present invention, further provided is a nucleic acid comprising at least 15 nucleotides which are equivalent to, complementary to, or hybridize under moderately stringent or stringent conditions to a sequence selected from the group consisting of SEQ ID Nos: 10 to 12, or complementary sequence thereof.

Preferably, the nucleic acid comprises a sequence which is equivalent to, complementary to, or hybridizes under moderately stringent or stringent conditions to a sequence selected from the group consisting of SEQ ID Nos: 1 to 9, or complementary sequence thereof.

In certain preferred embodiments, the nucleic acid is used as a primer and/or a probe for detecting the methylation level within at least one target region of RNF180 gene or fragment thereof.

According to another aspect of the present invention, further provided is a composition comprising the nucleic acid, further a reagent that converts 5-unmethylated cytosine base of a gene to uracil or other base that is detectably different from cytosine in terms of hybridization performance. Preferably, the reagent is bisulfite.

According to another aspect of the present invention, further provided is a kit comprising the composition described above. Typically, the kit comprises a container for containing a biological sample of a patient. Also, the kit can also comprise the instructions for using the kit and explaining the results of the kit.

In the present application, it is found through the experiments that there is great difference of the methylation level of RNF180 gene between gastritis and gastric cancer, and the content of RNF180 increases gradually from normal group, chronic superficial gastritis group, chronic atrophic gastritis (including chronic gastritis complicated with intestinal metaplasia) group, to gastric cancer groups stages I to IV, while the Ct value decreases gradually. The positive rate also increases gradually from normal group to gastric cancer groups in the same order. Therefore, the present application provides a method for grading gastric cancer and gastritis by measuring the methylation level of RNF180 gene in a sample to be tested, thereby providing a noninvasive and rapid method for screening gastric cancer and gastritis.

Septin9 and RNF180 are combined for detecting gastric cancer and associated with gastric cancer staging (I-IV). RNF180 could also be used to detect gastritis, and distinguish among normal group, gastritis group and gastric cancer group based on the significant statistical difference among the three groups. In addition, RNF180 could also be used to distinguish detectably the gastritis with intestinal metaplasia from common gastritis without intestinal metaplasia, and the positive rates of RNF180 of the gastritis with intestinal metaplasia is 100% and common gastritis is about 27%.

The present applicant also finds that the level of methylated RNF180 gene in peripheral blood tends to increase as age increases. However, since the elderly has a certain degree of gastritis more or less, it is difficult to distinguish whether age factor or gastritis factor leads to the elevated level of methylated RNF180 gene in peripheral blood, which has a significant impact on the specificity and reliability of detection of gastritis and gastric cancer. Therefore, taken this into consideration, Septin9 is introduced simultaneously into the detection. As the impact of age factor and gastritis factor on Septin9 gene can be ignored, Septin9 can be used to confirm the detection of gastric cancer. Specifically, about 40% of gastric cancer is simultaneously positive for both Septin9 and RNF180, and the doubel positives can be used as the criteria with the specificity of up to 90%. The methylation detection of Septin9 can overcome and compensate for the disadvantage of poor specificity when the methylation detection of RNF180 is used alone, so as to indicate the presence of abnormal cell proliferation more accurately. Also, according to certain specific embodiments, for some gastric cancers, RNF180 is negative, but Septin9 is positive, and these gastric cancers can be detected by Septin9 with the sensitivity increased by about 3%. The methylation detection of Septin9 can overcome and compensate for the disadvantage of poor sensitivity when methylation detection of RNF180 is used alone, so as to indicate the presence of abnormal cell proliferation more accurately. Thus, both the sensitivity and specificity for grading gastritis and gastric cancer can be improved by combining the two biomarkers, Septin9 and RNF180.

Finally, the simultaneous bi-channel detection of the two biomarkers, Septin9 and RNF180, can be conveniently achieved by utilizing a real-time PCR assay of DNA in a plasma sample, and whether a sample is positive or not can be quickly and easily determined according to the cycle threshold (Ct) value of a real-time PCR. The present invention provides a non-invasive and rapid method for grading cancer and inflammation.

Unless otherwise defined, the relevant technical and scientific terms in this specification are intended to be the same meaning as commonly understood by those skilled in the art. Although similar or identical methods and materials to those described herein can be applied in the experimental or practical applications, materials and methods are described herein below. In the case of conflict, reference is made to the specification including the definitions contained therein. In addition, the materials, methods and examples are illustrative only and not restrictive.

Other features and advantages of the present invention will be described in detail by the following detailed description and the claims.

BRIEF DESCRIPTION OF FIGURES

The above and other features of the present invention will be further described in conjunction with the following figures and their detailed description. It should be understood that these figures only show several exemplary embodiments in accordance with the present invention and should not be considered as the limitation of the scope of the present invention. Unless otherwise specified, the figures are not necessarily to be in proportion, and similar reference numbers refer to similar parts.

FIGS. 7A-7C show the comparation of RS19 positive rates between normal people, superficial, atrophic/intestinal metaplasia, and gastric cancer; the comparation of RS19 positive rates between gastric cancer stages I, II, III and IV; and a histogram of the average dCt values of RS19 of normal people, gastritis, and gastric cancer, respectively.

BEST MODES FOR CARRYING OUT INVENTION

Figure 1:
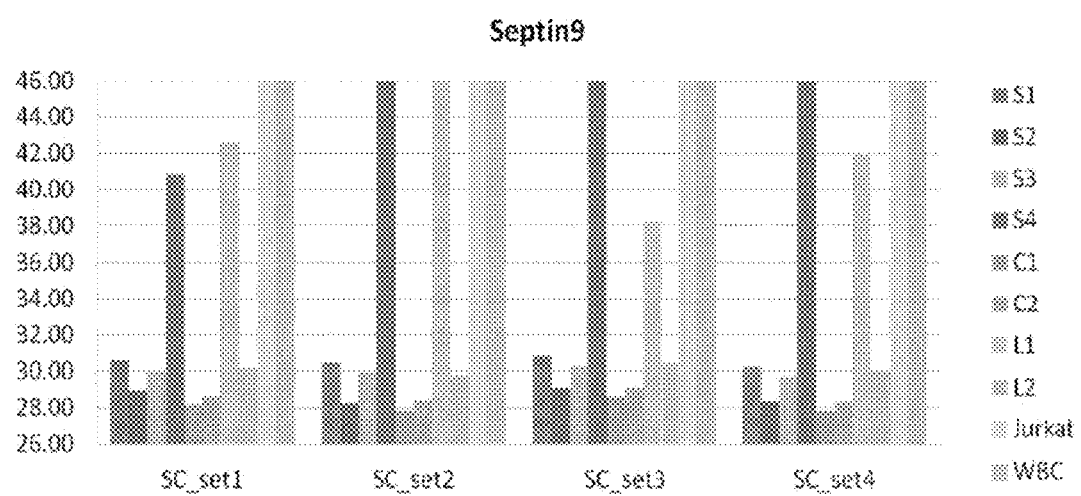
FIG. 1 shows that none of the four sets of primers and probes for RNF180 affects the determination of Septin9 in multiple detection of the methylated DNAs of Septin9 and RNF180.

Unless otherwise indicated, the implementation of the present application will employ the conventional techniques of molecular biology (including recombinant techniques), microbiology, cell biology, biochemistry, and genomics, all of which fall within the scopes of the conventional technical means in the art. Such techniques are described in detail in the literatures, such as Molecular Cloning: A Laboratory Manual, 2th Edition (Sambrook et al., 1989); Oligonucleotide Synthesis (M. J. Gait, 1984); Animal Cell Culture (R. I. Freshney, 1987); Methods in Enzymology series (American Academic Press, Inc.); Current Protocols in Molecular Biology (F. M. Ausubel et al., 1987, and updated periodically); PCR: The Polymerase Chain Reaction (Mullis et al., 1994). The primers, probes and kits used in the present application may be prepared according the standard techniques well known in the art.

Unless otherwise defined, the technical and scientific terms used in the present application have the same meaning as commonly understood by one of the ordinary skilled in the art to which the present invention belongs. Singleton et al., Dictionary of Microbiology and Molecular Biology, 2th Edition, J. Wiley & Sons (New York, N.Y. 1994), and March, Advanced Organic Chemistry Reactions, Mechanisms and Structure, 4th Edition, John Wiley & Sons (New York, N.Y. 1992), provide general guidance to those skilled in the art for a number of terms used in the present application.

Definitions

In the present application, "grading disease severity" means that the disease severity is determined based on detection results, and thus graded. According to the present application, the two levels, normal and cancer, can be distinguished according to the DNA methylation level, namely, a cancer in an individual can be detected. Preferably, according to the present application, the three levels, normal, inflammation and cancer, can be distinguished according to the DNA methylation level. For example, the three levels, normal, gastritis and gastric cancer, can be distinguished according to the methylation level of the DNAs to be measured in a sample from a patient, and for gastritis, it can be further divided into superficial gastritis and atrophic gastritis.

In the present application, "cancer" means and includes any malignancy, or malignant cell division or malignant tumour, or any condition comprising uncontrolled or inappropriate cell proliferation, and includes without limitation any disease characterized by uncontrolled or inappropriate cell proliferation.

In the present application, "gastric cancer" and "stomach cancer" have the same meaning and mean a cancer of stomach or of stomach cells. Such cancers may be adenocarcinomas that occur in the lining of stomach (mucosa) and may be in the pylorus, body or cardial (lower, body and upper) parts of stomach.

In the present application, "staging of gastric cancer" means that gastric cancer can be divided into four stages according to the clinical pathological staging standard of gastric cancer. The staging of gastric cancer involves three indexes: primary tumor (T), lymph node metastasis (N) and distant metastasis (M, including left supraclavicular lymph node metastasis, hematogenous metastasis and intraperitoneal implantation). "Stage I" refers to superficial gastric cancer without lymph node metastasis, or although the tumor has invaded muscle layer but not exceeded a half of a subregion; "stage II" refers to superficial cancer with a first station of lymph node metastasis, T2 cancer (tumor has invaded muscle layer of gastric wall but not exceeded a half of a subregion in size) and T3 cancer (tumor has invaded gastric wall serosa, or although the tumor has not invaded the serosa, but the size of the lesion has exceeded a half of a subregion but not more than a subregion), T3 cancer without lymph node metastasis also belongs to this stage; "stage III" refers to the tumor of various size with a second station of lymph node metastasis, or the tumor with only a first station of lymph node metastasis or of which, the tumor size is exceeded a subregion without lymph node metastasis; and "stage IV" refers to all tumors with a third station of lymph node metastasis or distant metastasis, regardless of tumor size.

In the present application, "gastric cancer cells" means the cells having characteristic of gastric cancer, and includes precancerous cells.

In the present application, "precancerous" means the cells which are in the early stage of conversion to cancer cells or which is predisposed for conversion to cancer cells. Such cells may show one or more phenotypic traits having characteristic of the cancerous cells.

In the present application, "gastritis" refers to the inflammation of gastric mucosa caused by any cause, often accompanied with epithelial damage and cell regeneration. Gastritis is one of the most common diseases in digestive system, and generally divided into acute gastritis and chronic gastritis according to the urgency degree of its clinical onset. Chronic gastritis is generally divided into the following types: the gastritis of which inflammatory lesions are relatively superficial and confined to the surface layer of gastric mucosa (not more than a third), known as "superficial gastritis"; and "ulcerative gastritis", of which the leisions have been developed into gastric ulcers; and "atrophic gastritis", of which inflammatory lesions spread to the whole gastric mucosa with atrophy of gastric gland. Among these, it is found in the pathological biopsy of the patients with atrophic gastritis that two lesions, "colonic incomplete intestinal metaplasia" and "atypical hyperplasia" in the gastric mucosa, may develop into gastric cancer. So-called intestinal metaplasia means that small intestinal or colonic gland appears in gastric mucosa glands, that is, intestinal gland migrates into stomach, which should not occur in normal conditions. The more the amount of intestinal metaplasia is, the higher the severity of the atrophy is. Superficial gastritis and ulcerative gastritis can be collectively referred as "mild gastritis"; and "atrophic gastritis" and "gastritis with intestinal metaplasia" can be collectively referred as severe gastritis.

In the present application, "biomarker" refers to a substance such as a gene as a variable related to a disease to be measured, which may serve as an indicator or predictor of the disease. A biomarker may be the parameter from which the presence or risk of a disease can be inferred, without the detection of the disease itself.

In the present application, "nucleic acid", "nucleic acid sequence" and the like refers to polynucleotides, which may be gDNA, cDNA or RNA, and single-stranded or double-stranded. The term also includes peptide nucleic acid (PNA), or any chemically DNA-like or RNA-like material. "cDNA" refers to a DNA which is copied from naturally occurring mRNA. "gDNA" refers to a genomic DNA. A combination of these materials can also be included (i.e., a recombinant nucleic acid in which a part is gDNA and another part is cDNA).

In the present application, "operably associated" and "operably linked" refers to functional bond to a nucleic acid sequence.

In the present application, "stringent hybridization conditions" and "high stringency" refer to the conditions under which a probe hybridizes to its target subsequence, typically in a complex mixture of nucleic acids. Stringent conditions are sequence-dependent and different in different circumstances. A longer sequence hybridizes specifically at a higher temperature. An extensive guidance on the hybridization of nucleic acids is found in Tijssen, Techniques in Biochemistry and Molecular Biology—Hybridization with Nucleic Probes, "Overview of principle of hybridization and strategy of nucleic acid experiment". Generally, stringent conditions are lower than the melting point (Tm) for a specific nucleic acid by about 5-10° C. at a defined ionic strength and pH. At a temperature of Tm (with defined ionic strength, pH, and concentration of nucleic acid), 50% of probes complementary to a target hybridize to a target sequence at equilibrium. Stringent conditions may also be achieved with the addition of a destabilizing agent. For a selective or specific hybridization, a positive signal is at least two times, preferably 10 times of background hybridization. Exemplary stringent hybridization conditions are as following: hybridizing at 42° C. in a solution of 50% formamide, 5×SSC, and 1% SDS, or hybridizing at 65° C. in a solution of 5×SSC, 1% SDS, then washing in a solution of 0.2×SSC and 0.1% SDS at 65° C.

Furthermore, nucleic acids that can not hybridize under stringent conditions are still substantially similar if the polypeptides which they encode are substantially similar. In this case, the nucleic acids typically hybridize under moderately stringent hybridization conditions. Exemplary "moderately stringent hybridization conditions" include hybridizing in a solution of 40% formamide, 1 M NaCl, 1% SDS at 37° C., and washing in a solution of 1×SSC at 45° C. Those of ordinary skill in the art can be readily taught from the prior art the conditions under which how to achieve identical stringency. For PCR, a temperature of about 36° C. is typical for amplification with low stringency, and an annealing temperature may range from 32° C. to 48° C. depending on primer length. For highly stringent PCR amplification, a temperature of about 62° C. is typical, and an annealing temperature of highly stringent hybridization can range from 50° C. to 65° C., depending on primer length and specificity. Typical cycle conditions for both amplifications with high and low stringency include a consecutive denaturation phase at 90° C.-95° C. for 30 sec-2 min., an consecutive annealing phase for 30 sec-2 min., and an consecutive extension phase at about 72° C. for 1-2 min. The tools and guidelines for amplification reactions with low and high stringency can obtained from the prior art.

In the present application, "oligonucleotide" refers to a molecule consisting of two or more nucleotides, preferably more than three nucleotides. Its exact size will depend upon many factors which, in turn, depend upon the ultimate function and use of oligonucleotide. In certain specific embodiments, an oligonucleotide may have a length of 10 to 100 nucleotides. In certain specific embodiments, an oligonucleotide may have a length of about 10 to 30 nucleotides, or may have a length of about 20 to 25 nucleotides. In some particular embodiments, an oligonucleotide having a shorter length may be suitable.

In the present application, "primer" means an oligonucleotide, whether occurring naturally as in a purified restriction digest or produced synthetically, which is capable of acting as a initiation point of synthesis when placed under conditions in which synthesis of a primer extension product, which is complementary to a nucleic acid strand, is induced, i.e., in the presence of nucleotides and an inducing agent such as a DNA or RNA polymerase and at a suitable temperature and pH. The primer may be either single-stranded or double-stranded and must be sufficiently long to prime the synthesis of the desired extension product in the presence of an inducing agent. The exact length of a primer will depend upon many factors, including temperature, primer source and method to be used. For example, for diagnostic and prognostic applications, depending on the complexity of a target sequence, oligonucleotide primers typically contain at least or more than about 10, or 15, or 20, or 25 or more nucleotides, although it may contain fewer or more nucleotides. The factors involved in determining the appropriate length of a primer are well known to a person skilled in the art.

In the present application, "primer pair" means a pair of primers which hybridize to the opposite strands of a target DNA molecule, or to the regions of a target DNA which flank a nucleotide sequence to be amplified.

In the present application, "primer site" means the region of a target DNA or other nucleic acid to which a primer hybridizes.

In the present application, "probe" with regard to a nucleic acid sequence is used in its ordinary sense to mean a selected nucleic acid sequence that can hybridise under specified conditions to a target sequence and may be used to detect the presence of such target sequence. It will be understood by those skilled in the art that in some instances probes may be also be used as primers, and primers may be used as probes.

In the present application, "DNA methylation" refers to the addition of a methyl group to the 5-position of cytosine (C), typically (but not necessarily) in the context of CpG (cytosine followed by guanine) dinucleotides. As used herein, "an increased methylation level" or "a significant methylation level" refers to the presence of at least one methylated C nucleotide in a DNA sequence where the corresponding C is not methylated in a normal control sample (such as a DNA sample extracted from a non-cancerous cell or tissue sample, or a DNA sample that has been subjected to a treatment of methylation on DNA residues), in some embodiments at least 2, 3, 4, 5, 6, 7, 8, 9, 10 or more Cs may be methylated at locations where the Cs are unmethylated in a control DNA sample.

In the embodiments, an alteration of DNA methylation can be detected by a number of different methods. The methods for detecting DNA methylation include, for example, an assay of methylation-sensitive restriction endonuclease (MSREs) by either southern or polymerase chain reaction (PCR) analysis, methylation specific or sensitive PCR (MS-PCR), methylation-sensitive single nucleotide primer extension (Ms-SnuPE), a high resolution melting (HRM) analysis, bisulifte sequencing, pyrosequencing, methylation-specific single-strand conformation analysis (MS-SSCA), combined bisulifte restriction analysis (CO-BRA), methylation-specific denaturing gradient gel electrophoresis (MS-DGGE), methylation-specific melting curve analysis (MS-MCA), methylation-specific denaturing high-performance liquid chromatography (MS-DHPLC), methylation-specific microarray (MSO). These assays can be either PCR analysis, quantitative analysis with fluorescence labelling or southern blot analysis.

In the present application, "determination of methylation" means any determination that confirms the methylation status of one or more CpG dinucleotide sequence(s) within a DNA sequence.

In the present application, "biological sample" or "sample" includes sections of tissues, such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissues, cultured cells, e.g. primary cultures, explants, and transformed cells, stool, urine, stomach biopsy tissues, etc. A biological sample is typically obtained from a eukaryotic organism, which may be a mammal, may be a primate and may be a human individual.

In the present application, "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cell, stomach tissue, etc.) among other factors. Representative biopsy techniques include, but are not limited to, excisional biopsy, incisional biopsy, needle biopsy, surgical biopsy, and bone marrow biopsy. Colonoscopy is also included. A wide range of biopsy techniques are well known to those skilled in the art who will choose from them and implement them with minimal experimentation.

In the present application, "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule. In addition, an isolated nucleic acid molecule can include an engineered nucleic acid molecule such as a recombinant or synthetic nucleic acid molecule. A nucleic acid molecule existing among hundreds to millions of other nucleic acid molecules within, for example, a nucleic acid library (e.g., a cDNA or genomic library) or a portion of a gel (e.g., agarose, or polyacrylamide) containing restriction-digested genomic DNA is not to be considered an isolated nucleic acid.

In the present application, "cell" may be isolated, may be comprised in a population of cells, may be in culture, or may be comprised in a living individual and may be a mammalian cell and may be a human cell. Similarly, "tissue" may comprise any number of cells and may be comprised in a living individual or may be isolated therefrom.

In the present application, "purified" or "substantially purified" with regard to nucleic acids or polypeptides means those separated from their natural environment so that they consitute at least about 75%, 80%, 85%, 90% or 95% of total nucleic acid or polypeptide or organic chemical in a given sample. Protein purity is assessed herein by SDS-PAGE and silver staining. Nucleic acid purity is assessed by agarose gel and EtBr staining.

In the present application, "detection" means any process of observing a marker, or a change in a marker (such as for example the change in the methylation status of a marker, or the expression level of a nucleic acid or protein sequences), in a biological sample, whether or not the marker or the change in the marker is actually detected. In other words, the act of probing a sample for a marker or a change in a marker is a "detection", even if the marker is determined to be not present or below the level of sensitivity. Detection may be a quantitative, semi-quantitative or non-quantitative observation and may be based on a comparison with one or more control samples. It will be understood that detecting a gastric cancer as disclosed herein includes detecting precancerous cells that are beginning to or will, or have an increased predisposition to develop into gastric cancer cells. Detecting a gastric cancer also includes determining possible probability of mortality or a likely prognosis for the condition.

In the present application, "homology", "identity" and "similarity" mean sequence similarity between two nucleic acid molecules. They can each be determined by comparing a position in each sequence which may be aligned for purposes of comparison.

When an equivalent position in the compared sequences is occupied by the same base, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, preferably less than 25% identity with a sequence of the present invention. In comparing two sequences, the absence of residues (amino acids or nucleic acids) or presence of extra residues also decreases the identity and homology/similarity. In specific embodiments, two or more sequences or subsequences may be considered substantially or significantly homologous, similar or identical if the identity between sequences are about 60%, or are about 65%, 70%, 75%, 80%, 85%, 90%, 91%, 92%, 93%, 94%, 95%, 96%, 97%, 98%, 99%, or more over a specified region, when compared and aligned for maximum correspondence over a comparison window or designated region, as measured using a BLAST or BLAST 2.0 sequence comparison algorithms with default parameters described below, or by manual alignment and visual inspection such as provided on-line by the National Center for Biotechnology Information (NCBI). This definition also refers to, or may be applied to, the compliment of a test sequence. Thus, to the extent allowed in the context herein, for example, if a nucleotide sequence can be predicted to be naturally occurring in a DNA duplex, or naturally occurring as one or two of complementary strands, the nucleotide sequence itself which is complementary to a specified target sequence or a variant thereof is considered to be "similar" to the target sequence, and when referring to a "similar" nucleic acid sequence, it includes a single stranded sequence, its complementary sequence, a double stranded chain complex, a sequence capable of encoding an identical or similar polypeptide product, and any permissible variants of any described above. The case where the similarity must be limited to the analysis of a single nucleic acid strand sequence may include, for example, the detection and quantification of the expression of a particular RNA sequence or encoding sequence in a cell. The definition also includes a sequence that has deletion and/or addition, as well as has a substitution. In the embodiments, identity or similarity exists over a region of at least about 10, 11, 12, 13, 14, 15, 16, 17, 18, 19, 20, 21, 22, 23, 24, 25 or more nucleotides in length, or over a region of more than about 10, 15, 20, 25, 30, 35, 40, 45, 50, 55, 60, 65, 70, 75, 80, 85, 90, 95 or more than 100 nucleotides in length.

In the present application, "amplification" means a process whereby multiple copies are obtained from one specific locus of a nucleic acid, such as a genomic DNA or cDNA. Amplification can be accomplished by any one of a number of known means, including but not limited to a polymerase chain reaction (PCR), transcription-based amplification and strand displacement amplification (SDA).

In the present application, "standard amplification conditions" refers to the basic components of an amplification reaction mixture and cycling conditions that include multiple cycles of denaturing template nucleic acid, annealing the oligonucleotide primers with template nucleic acid, and extending primers by a polymerase to produce an amplification product.

In the present application, "polymerase chain reaction" or "PCR" means a technique in which cycles of denaturation, annealing with primers, and extension with a DNA polymerase are used to amplify the number of copies of a target DNA sequence by approximately $10^6$ times or more. A polymerase chain reaction process for amplifying nucleic acid is found in U.S. Pat. Nos. 4,683,195 and 4,683,202.

In the present application, "fluorescence-based real-time PCR" means a method in which a fluorophore is added to a PCR reaction system to monitor the progress of a whole PCR process in real time by fluorescence signal accumulation, and an unknown template is quantitatively analyzed by a standard curve. In the PCR technique, there is a very important concept, i.e., cycle threshold, also known as Ct value. C represents cycle, and t represents threshold (critical value). Ct value means that the number of cycles experienced when the fluorescence signal in each reaction tube reaches the set threshold value. For example, a fluorescence threshold is set as follow: the fluorescence signal of the first 15 cycles of a PCR reaction is used as the fluorescence background signal and the default setting of the fluorescence threshold is 10 times of the standard deviation of the fluorescence signal from 3 to 15 cycles.

In the present application, "cut-off value of real-time PCR" represents one critical Ct value for determining that a given sample is positive or negative for one certain biomarker. According to certain specific embodiments of the present application, the "critical Ct value (cut off value)" is obtained according to a certain number of sample data and based on a statistical treatment, which may vary depending on the desired sensitivity or specificity requirements. In the summary, this critical Ct value will be further illustrated.

In the present application, "sensitivity" means the ratio of cancers detected from certain cancer samples and is calculated as: Sensitivity=(detected cancers/all cancers), and "specificity" means the ratio of normal detected from certain normal samples and is calculated as: Specificity=(undetected negatives/total negatives).

In the present application, "label" or "detectable moiety" is a component detectable by spectroscopic, photochemical, biochemical, immunochemical, chemical, or other physical means. For example, useful labels include 32P, fluorescent dyes, electron-dense reagents, enzymes (e.g., those commonly used in an ELISA), biotin, digoxigenin, or haptens and proteins which can be made detectable, e.g., by incorporating a radiolabel into a peptide or antibodies used to detect specifical reaction with a peptide.

Nucleic acid molecules can be detected using a number of different methods. Methods for detecting nucleic acids include, for example, PCR and nucleic acid hybridizations (e.g., Southern blot, Northern blot, or in situ hybridizations). Specifically, oligonucleotides (e.g., oligonucleotide primers) capable of amplifying a target nucleic acid can be used in a PCR reaction. PCR methods generally include the steps of obtaining a sample, isolating nucleic acid (e.g., DNA, RNA, or both) from the sample, and contacting the nucleic acid with one or more oligonucleotide primers that hybridize(s) with specificity to the template nucleic acid under conditions under which amplification of the template nucleic acid can occur. In the presence of a template nucleic acid, an amplification product is produced. Conditions for amplification of a nucleic acid and detection of an amplification product are known to those of skill in the art. A range of modifications to the basic technique of PCR also have been developed, including but not limited to anchor PCR, RACE PCR, RT-PCR, and ligation chain reaction (LCR). A pair of primers in an amplification reaction must anneal to opposite strands of the template nucleic acid, and should be an appropriate distance from one another such that the polymerase can effectively polymerize across the region and such that the amplification product can be readily detected using, for example, electrophoresis. Oligonucleotide primers can be designed using, for example, a computer program such as OLIGO (Molecular Biology Insights Inc., Cascade, Colo.) to assist in designing oligonucleotide primers that have similar melting temperatures. Typically, oligonucleotide primers are 10 to 30 or 40 or 50 nucleotides in length (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length), but can be longer or shorter if appropriate amplification conditions are used.

Detection of an amplification product or a hybridization complex is usually accomplished using detectable labels.

The term "label" with regard to a nucleic acid is intended to encompass direct labeling of a nucleic acid by coupling (i.e., physically linking) a detectable substance to the nucleic acid, as well as indirect labeling of the nucleic acid by reactivity with another reagent that is directly labeled with a detectable substance. Detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin. An example of indirect labeling includes end-labeling a nucleic acid with biotin such that it can be detected with fluorescently labeled streptavidin.

SUMMARY

The present application provides a detection method for a cancer by combining Septin9 and RNF180 genes, and the corresponding composition, kit and nucleic acid sequences, for non-invasive diagnosis and detection of a cancer with high efficiency and sensitivity. It has been found according to the specific embodiments that the combination of Septin9 and RNF180 greatly improves the sensitivity or specificity of detection of a cancer, particularly of gastric cancer.

The present application also provides a method for grading disease severity by RNF180 gene, preferably a combination of Septin9 and RNF180 genes, as well as the corresponding composition, kit and nucleic acid sequences, so that a cancer and inflammation, especially gastric cancer and gastritis be can be graded efficiently and sensitively in a noninvasive manner.

The followings are the examples of the composition, kit, nucleic acid sequences, and detection methods of the present application. It will be understood that a variety of other embodiments could be implemented in view of the general description provided above.

In the first group of embodiments, a composition for diagnosing or detecting abnormal cell proliferation in a biological sample is disclosed, which includes a nucleic acid for detecting the methylation level within at least one target region of Septin9 and RNF180 genes or fragments thereof. In particular, the composition comprises not only a nucleic acid sequence for detecting the methylation level within at least one target region of Septin9 gene or fragment thereof, but also a nucleic acid sequence for detecting the methylation level within at least one target region of RNF180 gene or fragment thereof.

The present application also discloses a composition for grading disease severity in an individual, which comprises a nucleic acid for detecting the methylation level within at least one target region of RNF180 gene or fragment thereof, so as to grade disease severity based on the detection result of the methylation of RNF180. Preferably, the composition comprises not only a nucleic acid sequence for detecting the presence or absence of methylation within at least one target region of RNF180 gene or fragment thereof, but also a nucleic acid sequence for detecting the presence or absence of methylation within at least one target region of Septin9 gene or fragment thereof.

In the following, Septin9 gene will be introduced firstly. Human Septin9 gene (also known as MLL septin-like fusion protein, MLL septin-like fusion protein MSF-A, Slpa, Eseptin, Msf, septin-like ovarian/breast septin (Ov/Brseptin), and Septin D1), which is is a member of the Septin gene family, located within contig AC068594.15.1.168501 of chromosome 17q25. For example, SEQ ID No: 13 provides a sequence of promoter region of Septin9 which is rich in CpG.

The sequence of SEQ ID No: 13 is as follow:

```
CGTTACCCGAGTTGTAAAGGGCGGCTCCCTGTGTCTGCCCCGCTGCACCG
ATACACCGAGCTGCGCACGGTGCCCAGCGCAGGGAGAACAAATGATCATC
TGTCCAACGCGCCCATTTACAGGTGAGGAAACTAAGGCTCCAACTCAATC
GACGCACTCTGCCCTTTTGATTACCAGAAAAGTAGCAGGACAGGTGTCCT
GTCCCGCCCTACCCCGGCCCACTAAGCCGGCACCCCGGCTCCGACCCCCG
GCTGTGCCCGGCGCCGCCGCGGTGCCCGGCGCCGCCGCCTCGCCCGGCGG
GGCCGCCCGGAGCGCCCGCACCTCCGCCCGCTTCCACCTGGCCGGGCCCG
CCCCGCCCGGACTCGGGACTGGGAAGTGCGGCGACTCCCGGAACCAGCCA
TTGGCGCCAGCGCGGGGAGCTGGGGGTGCAGAGCTGCGGGCGCGGCGGGC
CACGCAGGCGGCCCCCACCCCCGGCCTGGCCTGGTCTGGTCTGGTCTGCG
CTGCCGCGCGGGGGCGCCCCCTCCCAGGCCCGGCGCCCGCCAGCCCCGCT
CCGCCAGGTGCAGCGCAGCGCAGGGGTGGGCGGGGTGGGGCTCGGCGCG
CACGTTCACGGGGCGGGAGGGGCGGGTCAGGGGCGGGACCACAGCCGG
CTGGGCCGGGGTTCTATGCGCATCTCCGGGGAGGGGCGGGGCGGGGCGG
GGCCGGGGCGGGGCCCGGTCGGTGCACTCCAGACGGCGGGCCGCCCCCTC
TTCCCGCCTTCCTACTACCGGCCCAGGATTAGCGCCCTGGGAGCGCGCGC
CCCGCTGCCTCGCCGCCACACTTTCCTGGGAGCGGCGGCCACGGAGGCAC
CATGAAGAAGTCTTACTCAGGTGGGCTTCGCGCCCGGGGTGGGAGGGGT
CGGTGTCCCGGGACCAGCGCTGCTCACCTGAGTGCCTGCGGCCGGGAGTG
GCGAGGCGCCCCCGGAGCTGAGCGAGTCCCCGCGGCGGGCACACTGCAGG
TCGAGTTCCTCCCAGGACAGGGCCGCTGTCGGGCCGCTTTCGACCTGAGC
CGACCGTCCCCTGCGCTGTCTCCAGCCCTTGCTCGAGTGTCGGAGGGGCT
GCCCTGGGGGACGCTCCCTCTTCCTCGCCCCTTGCACCCTCGCAGGAATC
GCTGACTTTCCAGGTCGGCCGGGTGCTTTGGGTCCCTGTGCGTCTGTGTG
GGTGAATGGGGTCGGGGCTAGGTGGAGGGGTGTCCTTGGGTTCAGCCTCT
AGGGCTGGTGGTCCAGGCCGCAGCATCCTTTCTTCGGATTCTCTTCGGTT
TCTCCTCTACTTAGTGGGGCACGGGACGGCCTCCAGATGGGACCGTCCAG
CAGCGCCCAAACTTGGCGACTCGGGTTCACGTTTTGCGCTCAGGACGCCG
CCCGC
```

The members of the Septin gene family are involved in multiple cellular functions ranging from vesicular transport to cytokinesis. The destructive effect on Septin 9 results in incomplete cell division, and Septin 9 and other proteins have been shown to be fusion partners of protooncogene MLL, indicating their roles in tumorigenesis.

The nucleic acid sequence for detecting the presence or absence of methylation within at least one target region of Septin9 gene or fragment thereof comprises a long fragment of at least 9 bases which is equivalent to, complementary to, or hybridizes under moderately stringent or stringent conditions to a contiguous sequence selected from SEQ ID No: 13.

According to a specific embodiment, the nucleic acid sequence for detecting the presence or absence of methylation within at least one target region of RNF180 gene or fragment thereof may comprises at least 15 nucleotides which are equivalent to, complementary to, or hybridize under moderately stringent or stringent conditions to SEQ ID No: 10 as shown below, or complementary sequence thereof, and SEQ ID No: 10 represents the promoter region of RNF180 and correspondes to Genbank accession number: NMi001113561 chr51 63497153-63497758. The underlined indicates the "transcription initiation site".

According to certain preferred embodiments, the primers and probes can be designed based on the sequence of SEQ ID No: 10. The sequences suitable for serving as the primers and probes for PCR amplification may comprise nucleotides of any suitable length, e.g., may comprise at least 15 nucleotides, or may comprise at least 20, 25, 30, 35, 40, 45, or more than 50 nucleotides. In these specific embodiments, the nucleic acid sequence may have similarity of approximately 95%, 96%, 97%, 98%, or 99% to the sequence of SEQ ID No: 10 or complementary sequence thereof.

```
(-234 bp to +372 bp with respect to the transcrip-
tion initiation site)
                                      SEQ ID No: 10
GATAATTTCTGTGGCTCTGGTAAGGGGATGACAAGGGAGAAAAACTTTCC

CACGGTTCCGTCTGGCCCGCGGCGCTTGTCTGCCTGCGCGGGGTCAAAGC

CCGGCGCCGCCCACGCGCGGCTCGGGTGGGAACCCGCAGACGTGGGGCGA

GCAGGGCCGCTGGCTGTGGCGGGCGAGCGCCGGGGCGCCACGTCCGAGGC

CGCGGGGTCGGGGCTGCAGGCACAGCTCGAGCGCTTTCCGCGGGGTTTGG

CTCCTGTCGCTTCCCGTCTCGCCGAACCGGCATCGCCGCCGCCGGAGCCG

CAGCGAGTCCTCAGAGCCTGGCTGCTGGCGGCCGGGAGCGCCGGGACGGG

GCGCGAAGCCGGAGGCTCCGGGACGTGGATACAGGTAAAGGCCGGCGGGT

CGGAGTCGGGCGGGGCGCGGCGGCGGCGCCTCTCGGAGGGACCTGGCCTC

GGCCGGGCCCTACCCAGCCGCGGTGGCCCGGGCCCCACGTTGGCCCAGG

CGGGGACGTGCCAAGGGGCTGGGCTAGGGTTGCCGCTGGCCTGGCCGCCT

CTCGCCCGGCGGGCCTCAGGTGACGCGGCCGCGGCTTAACTTTCGCACCT

GAGGCT
```

Preferably, the nucleic acid sequence used to detect the presence or absence of methylation within at least one target region of RNF180 gene or fragment thereof comprises at least 15 nucleotides which are equivalent to, complementary to, or hybridize under moderately stringent or stringent conditions to SEQ ID No: 11 shown below, or complementary sequence thereof.

```
(-167 bp to +135 bp with respect to the transcrip-
tion initiation site)
                                      SEQ ID No: 11
CGCGGCGCTTGTCTGCCTGCGCGGGGTCAAAGCCCGGCGCCGCCCACGCG

CGGCTCGGGTGGGAACCCGCAGACGTGGGGCGAGCAGGGCCGCTGGCTGT

GGCGGGCGAGCGCCGGGGCGCCACGTCCGAGGCCGCGGGGTCGGGGCTGC

AGGCACAGCTCGAGCGCTTTCCGCGGGGTTTGGCTCCTGTCGCTTCCCGT

CTCGCCGAACCGGCATCGCCGCCGCCGGAGCCGCAGCGAGTCCTCAGAGC

CTGGCTGCTGGCGGCCGGGAGCGCCGGGACGGGGCGCGAAGCCGGAGGCT

CC
```

Further preferably, the nucleic acid sequence used to detect the presence or absence of methylation within at least one target region of RNF180 gene or fragment thereof comprises at least 15 nucleotides which are equivalent to, complementary to, or hybridize under moderately stringent or stringent conditions to SEQ ID No: 12 shown below, or complementary sequence thereof.

```
(-43 bp to +135 bp with respect to the trancsrip-
tion initiation site)
                                      SEQ ID No: 12
GTCCGAGGCCGCGGGGTCGGGGCTGCAGGCACAGCTCGAGCGCTTTCCGC

GGGGTTTGGCTCCTGTCGCTTCCCGTCTCGCCGAACCGGCATCGCCGCCG

CCGGAGCCGCAGCGAGTCCTCAGAGCCTGGCTGCTGGCGGCCGGGAGCGC

CGGGACGGGGCGCGAAGCCGGAGGCTCC
```

Therefore, TaqMan probes and primers can be designed to detect the DNA methylation of the promoter region of RNF180 gene (-234 bp to +372 bp with respect to the transcription initiation site), preferably the promoter region to be detected is -167 bp to +135 bp with respect to the transcription initiation site, more preferably the promoter region to be detected is -43 bp to +135 bp with respect to the transcription initiation site. The length of an amplicon for detection ranges from 66 bp to 130 bp.

For example, in certain specific embodiments, the primers and probes are designed to detect the presence or absence of methylation within at least one target region of RNF180 gene or fragment thereof with SEQ ID No: 12 (-43 bp to +135 bp with respect to the transcription initiation site) as the target region. Therefore, a variety of combinations of probes and primers can be designed according to the present application, and each combination of probes and primers may be different in terms of performance. Therefore, in order to screen the primers and probes with high efficiency, the present application utilizes an artificially methylated template and an unmethylated template, as well as cancer (e.g., gastric cancer) and normal DNA as templates, to screen the multiple designed combinations of probes and primers by the following steps:

1. designing the primers and probes for the promoter region of RNF180 gene;
2. designing an artificially methylated DNA and an unmethylated DNA;
3. screening the primers and probes with the artificially methylated DNA and the unmethylated DNA, wherein the artificially methylated DNA is amplified, while the artificially unmethylated DNA is not amplified;
4. screening the primers and probes from the DNA extracted from normal leukocyte DNA.
5. screening the primers and probes with the DNA extracted from human gastric cancer tissue if there is little or no amplification of the DNA extracted from of normal leukocytes.
6. screening the primers and probes from the DNA extracted from normal plasma at clinical study phase;

7. screening the primers and probes with the DNA extracted from the patients with gastric cancer if there is little or no amplification in normal plasma at clinical study phase.

Through the screening described above, the following sequences of SEQ ID Nos: 1-9 are constructed as primers and probes:

```
Primer:
(180F7)
                                         SEQ ID No: 1
5'-GTTCGAGGTCGCGGGGTC-3'

Probe:
(180P7)
                                         SEQ ID No: 2
5'-CAL Fluor Red-
AACGCTCGAACTATACCTACAACCCC-BHQ2-3'

Primer:
(180R7)
                                         SEQ ID No: 3
5'-ACAAAAACCAAACCCCGCG-3'

Primer:
(180F24)
                                         SEQ ID No: 4
5'-GCGGGGTTTGGTTTTTGT-3'

Probe:
(180P2)
                                         SEQ ID No: 5
5'-AL Fluor Red-CCGACGACGACGATACCG-
BHQ2-3'

Primer:
(180R2)
                                         SEQ ID No: 6
5'-ACAACCAAACTCTAAAAACTCG-3'

Probe:
(180P14)
                                         SEQ ID No: 7
5'-CAL Fluor Red-CGTCGGAGTCGTAGCGAGTTT-
BHQ2-3'

Primer:
(180R135)
                                         SEQ ID No: 8
5'-AAAACCTCCAACTTCACACCC-3'

Primer:
(180R14)
                                         SEQ ID No: 9
5'-CGCCAACAACCAAACTCTAA-3'
```

Further, the present applicant has designed at least one Primers and probes combination based on the screened primers and probes described above, among which the following four combinations are preferrable:

```
A. Primers and probes combination 1 (amplicon
66 bp, -43 bp to +23 bp with respect to the
trancription initiation site)
(180F7)
                                         SEQ ID No: 1
5'-GTTCGAGGTCGCGGGGTC-3'

(180P7)
                                         SEQ ID No: 2
5'-CAL Fluor Red-
AACGCTCGAACTATACCTACAACCCC-BHQ2-3'

(180R7)
                                         SEQ ID No: 3
5'-ACAAAAACCAAACCCCGCG-3'

B. Primers and probes combination 2 (amplicon
86 bp, +5 bp to +91 bp with respect to the
transcription initiation site)
(180F24)
                                         SEQ ID No: 4
5'-GCGGGGTTTGGTTTTTGT-3'

(180P2)
                                         SEQ ID No: 5
5'-CAL Fluor Red-CCGACGACGACGATACCG-BHQ2-3'

(180R2)
                                         SEQ ID No: 6
5'-ACAACCAAACTCTAAAAACTCG-3'

C. Primers and probes combination 3 (amplicon
130 bp, +5 bp to +135 bp with respect to the
transcription initiation site)
(180F24)
                                         SEQ ID No: 4
5'-GCGGGGTTTGGTTTTTGT-3'

(180P14)
                                         SEQ ID No: 7
5'-CAL Fluor Red-CGTCGGAGTCGTAGCGAGTTT-BHQ2-
3'

(180R135)
                                         SEQ ID No: 8
5'-AAAACCTCCAACTTCACACCC-3'

D. Primers and probes combination 4 (amplicon
91 bp, +5 bp to +96 bp with respect to the
transcription initiation site)
(180F24)
                                         SEQ ID No: 4
5'-GCGGGGTTTGGTTTTTGT-3'

(180P14)
                                         SEQ ID No: 7
5'-CAL Fluor Red-CGTCGGAGTCGTAGCGAGTTT-BHQ2-
3'

(180R14)
                                         SEQ ID No: 9
5'-CGCCAACAACCAAACTCTAA-3'
```

The sites of the above-described combinations of primers and probes binding to the above-described gene sequences are further illustrated below (wherein the underlined by the lines of the same type indicates the corresponding parts).

A. Primers and probes combination 1 (amplicon 66 bp, −43 bp to +23 bp with respect to the transcription initiation site)

GATAATTTCTGTGGCTCTGGTAAGGGGATGACAAGGGAGAAAAACTTTCC

CACGGTTCCGTCTGGCCCGCGGCGCTTGTCTGCCTGCGCGGGTCAAAGC

CCGGCGCCGCCCACGCGCGGCTCGGGTGGGAACCCGCAGACGTGGGGCG

The schematic diagram of the binding sites:

```
(180F7)
                                         SEQ ID No 1
5'-GTTCGAGGTCGCGGGGTC-3'

AGCAGGGCCGCTGGCTGTGGCGGGCGAGCGCCGGGGCGCCACGTCCGAGG

CCGCGGGGTCGGGGCTGCAGGC
```

```
(180P7)
                                                  SEQ ID No 2
5'-CAL Fluor Red-
AACGCTCGAACT
ATACCTACAACCCC-BHQ2-3'
ACAGCTCGAGCGCTTTCCGCGGGGTTTGGCTCCTGTCGCTTCCCGTCTCG
CCGAACCGGCATCGCCGCCGCCGGAG (180R7)
                                                  SEQ ID No 3
5'-ACAAAAACCAAACCCCGCG-3'
CCGCAGCGAGTCCTCAGAGCCTGGCTGCTGGCGGCCGGGAGCGCCGGGAC
GGGGCGCGAAGCCGGAGGCTCCGGGACGTGGATACAGGTAAAGGCCGGCG
GGTCGGAGTCGGGCGGGCGCGGCGGCGGCGCCTCTCGGAGGGACCTGGC
CTCGGCCGGGCCCTACCCAGCCGCGGTGGCCCGGGCCCCACGTTGGCCC
AGGCGGGGACGTGCCAAGGGGCTGGGCTAGGGTTGCCGCTGGCCTGGCCG
CCTCTCGCCCGGCGGGCCTCAGGTGACGCGGCCGCGGCTTAACTTTCGCA
CCTGAGGCT
```

B. Primers and probes combination 2 (amplicon 86 bp, +5 bp to +91 bp with respect to the transcription initiation site)

```
GATAATTTCTGTGGCTCTGGTAAGGGGATGACAAGGGAGAAAAACTTTC
CCACGGTTCCGTCTGGCCCGCGGCGCTTGTCTGCCTGCGCGGGGTCAAA
GCCCGGCGCCGCCCACGCGCGGCTCGGGTGGGAACCCGCAGACGTGGGG
CGAGCAGGGCCGCTGGCTGTGGCGGGCGAGCGCCGGGGCGCCACGTCCG
AGGCCGCGGGGTCGGGGCTGCAGGC
```

The schematic diagram of the binding sites:

```
BHQ2-3'
(180F24)
                                                  SEQ ID No 4
5'-GCGGGGTTTGGTTTTTGT-3'
(180P2)
                                                  SEQ ID No 5
5'-CAL Fluor Red-CCGACGACGACGATACCG-
ACAGCTCGAGCGCTTTCCGCGGGGTTTGGCTCCTGTCGCTTCCCGTCTCG
CCGAACCGGCATCGCCGCCGCCGGAG
CCGCAGCGAGTCCTCAGAGCCTGGCTGCTGGCGGCCGGGAGCGCCGGGA
CGGGGCGCGAAGCCGGAGGCTCCG (180R2)
                                                  SEQ ID No 6
5'-ACAACCAAACTCTAAAAACTCG-3'
GGACGTGGATACAGGTAAAGGCCGGCGGGTCGGAGTCGGGCGGGGCGCGG
CGGCGGCGCCTCTCGGAGGGACCTGGCCTCGGCCGGGCCCTACCCAGCCG
CGGTGGCCCGGGCCCCACGTTGGCCCAGGCGGGGACGTGCCAAGGGGCT
GGGCTAGGGTTGCCGCTGGCCTGGCCGCCTCTCGCCCGGCGGGCCTCAGG
TGACGCGGCCGCGGCTTAACTTTCGCACCTGAGGCT
```

C. Primers and probes combination 3 (amplicon 130 bp, +5 bp to +135 bp with respect to the transcription initiation site)

```
GATAATTTCTGTGGCTCTGGTAAGGGGATGACAAGGGAGAAAAACTTTCC
CACGGTTCCGTCTGGCCCGCGGCGCTTGTCTGCCTGCGCGGGGTCAAAGC
CCGGCGCCGCCCACGCGCGGCTCGGGTGGGAACCCGCAGACGTGGGGCG
AGCAGGGCCGCTGGCTGTGGCGGGCGAGCGCCGGGGCGCCACGTCCGAGG
CCGCGGGGTCGGGGCTGCAGGC
```

The schematic diagram of the binding sites:

```
(180F24)
                                                  SEQ ID No 4
5'-GCGGGGTTTGGTTTTTGT-3'
(180P14)
                                                  SEQ ID No 7
5'-CGTCGGAG
ACAGCTCGAGCGCTTTCCGCGGGGTTTGGCTCCTGTCGCTTCCCGTCTCG
CCGAACCGGCATCGCCGCCGCCGGAG
TCGTAGCGAGTTT-BHQ2-3'
CCGCAGCGAGTCCTCAGAGCCTGGCTGCTGGCGGCCGGGAGCGCCGGGA
CG GGGCGCGAAGCCGGAGGCTCC G
(180R135)
                                                  SEQ ID No 8
5'-AAAACCTCCAACTTCACACCG-3'
GGACGTGGATACAGGTAAAGGCCGGCGGGTCGGAGTCGGGCGGGGCGCGG
CGGCGGCGCCTCTCGGAGGGACCTGGCCTCGGCCGGGCCCTACCCAGCCG
CGGTGGCCCGGGCCCCACGTTGGCCCAGGCGGGGACGTGCCAAGGGGCT
GGGCTAGGGTTGCCGCTGGCCTGGCCGCCTCTCGCCCGGCGGGCCTCAGG
TGACGCGGCCGCGGCTTAACTTTCGCACCTGAGGCT
```

D. Primers and probes combination 4 (amplicon 91 bp, +5 bp to +96 bp with respect to the transcription initiation site)

```
GATAATTTCTGTGGCTCTGGTAAGGGGATGACAAGGGAGAAAAACTTTCC
CACGGTTCCGTCTGGCCCGCGGCGCTTGTCTGCCTGCGCGGGGTCAAAGC
CCGGCGCCGCCCACGCGCGGCTCGGGTGGGAACCCGCAGACGTGGGGCG
AGCAGGGCCGCTGGCTGTGGCGGGCGAGCGCCGGGGCGCCACGTCCGAG
GCCGCGGGGTCGGGGCTGCAGGC
```

The schematic diagram of the binding sites:

```
(180F24)
                                                  SEQ ID No 4
5'-GCGGGGTTTGGTTTTTGT-3'
```

-continued (180P14)

SEQ ID No 7

5'-<u>CGTCGGAG</u>

ACAGCTCGAGCGCTTTCC<u>GCGGGG</u>TTTGGCTCCTGT CGCTTCCCGTCTCG

CCGAACCGGCATCGCCGC<u>CGCCGGAG</u>

<u>TCGTAGCGAGTTT</u>-BHQ2-3'

<u>CCGCAGCGAGTCCTCAGAGCCTGGCTGCTGGCC</u>GCCGGGAGCGCCGGGAC

GGGGCGCGAAGCCGGAGGCTCCG (180R14)

SEQ ID No 9

5'-<u>CGCCAACAACCAAACTCTAA</u>-3'

GGACGTGGATACAGGTAAAGGCCGGCGGGTCGGAGTCGGGCGGGGCGCGG

CGGCGGCGCCTCTCGGAGGGACCTGGCCTCGGCCGGGCCCTACCCAGCCG

CGGTGGCCCGGGCCCCCACGTTGGCCCAGGCGGGGACGTGCCAAGGGGCT

GGGCTAGGGTTGCCGCTGGCCTGGCCGCCTCTCGCCCGGCGGGCCTCAGG

TGACGCGGCCGCGGCTTAACTTTCGCACCTGAGGCT

In certain specific embodiments, the composition further comprises a reagent that converts 5-unmethylated cytosine base of a gene to uracil or other base that is detectably different from cytosine in terms of hybridization performance. For example, the reagent may be bisulfite.

In certain specific embodiments, the abnormal cell proliferation is a cancer. For example, the abnormal cell proliferation is gastric cancer.

In certain specific embodiments, the disease severity is divided into three levels, wherein the first level is normal, the second level is inflammation and the third level is cancer. Preferably, the inflammation is gastritis, and the cancer is gastric cancer.

Further, for the use described or suggested above in the present application, in the second group of embodiments, disclosed is a kit which comprises the composition for diagnosing or detecting a biological sample as disclosed in the first group of embodiments. The description of the composition is similar to that of the first group of embodiments and will not be repeated herein.

Such a kit may include a supporter which is divided for hermetically accommodating one or more containers, such as vials, tubes, etc., and each container comprises a separate element to be used in the method. For example, one of the containers may comprise probes which are or may be detectably labeled.

Typically, the kit of the present application will comprise a container for containing a biological sample of a patient and the instructions for using the kit and explaining the results of the kit, and particularly, the kit of the present application comprises the materials as required from a commercial and user's perspective, i.e, a container for containing a biological sample of a patient, a buffer, a diluent, a filter, a needle, a syringe, and instructions inserted in a package. A label may be used on the container to indicate that the components are used for a particular therapeutic or non-therapeutic application, and can also be used in vivo or in vitro, such as those described above.

There is a variety of embodiments for the kit of the present application. A typical embodiment is a kit which comprises a container, a label on the container, and components within the container; wherein the components comprise a nucleic acid for detecting the methylation level within at least one target region of Septin9 and RNF180 genes or fragments thereof. The label on the container indicates that the methylation level of the DNA of a sample can be evaluated with the components and the instructions on how to use the kit. The kit may further comprise a set of instructions and materials for preparing tissue sample and applying the composition of the present application to the sample. The kit may comprise a reagent which converts 5-unmethylated cytosine base of a gene to uracil or other base that is detectably different from cytosine in terms of hybridization performance, such as bisulfite.

In the third group of embodiments, disclosed is a method for detecting abnormal cell proliferation in an individual, comprising determining the methylation level within at least one target region of RNF180 and Septin9 genes or fragment thereof in a biological sample isolated from the individual, and detecting the abnormal cell proliferation in the individual by combining the detection results of the methylation of RNF180 and Septin9.

The present application also discloses a method for grading disease severity in an individual, comprising determining the methylation level within at least one target region of RNF180 gene or fragment thereof in a biological sample isolated from the individual, and grading disease severity by the detection result of the methylation of RNF180. Preferably, the method further comprises determining the methylation level within at least one target region of Septin9 gene or fragment thereof in a biological sample isolated from the individual, and grading the disease severity by combining the detection results of methylation of RNF180 and Septin9.

Typically, the method according to the present application further comprises the step of using a reagent to convert 5-unmethylated cytosine base of a gene to uracil or other base that is detectably different from cytosine in terms of hybridization performance.

Bisulfite modification of DNA is a known tool used to assess CpG methylation status. 5-methylcytosine is the most common covalent base modification in a DNA of a eukaryotic cell, and plays a role, for example, in transcriptional regulation, in genetic imprinting, and in tumorigenesis. Therefore, the identification of 5-methylcytosine as a component of genetic information is of considerable significance. However, 5-methylcytosine cannot be identified by sequencing, because 5-methylcytosine has the same base pairing behavior as cytosine. Moreover, the epigenetic information carried by 5-methylcytosine is completely lost during, e.g., PCR amplification.

The most frequently used method for analyzing DNA for the presence of 5-methylcytosine is based upon the specific reaction of bisulfite with cytosine whereby upon subsequent alkaline hydrolysis, cytosine is converted to uracil which corresponds to thymine in its base pairing behavior. However, it is noted that 5-methylcytosine remains unmodified under these conditions. Consequently, an original DNA is converted in such a manner that methylcytosine, which originally could not be distinguished from cytosine by its hybridization behavior, can now be detected as the only remaining cytosine using conventional and known molecular biological techniques, for example, by amplification and hybridization. All of these techniques are based on differential base pairing properties, which can now be fully exploited.

Therefore, typically, the present invention provides use of bisulfite technique, in combination with one or more methylation assays, for determination of the methylation status of CpG dinucleotide sequences within Septin9 and RNF180 gene sequences. Genomic CpG dinucleotides can be methylated or unmethylated (alternatively known as up- and down-methylated respectively). However, the methods of the present invention are suitable for the analysis of a heterogeneous biological sample, e.g., a low concentration of tumor cells within blood or stool. Accordingly, when analyzing the methylation level at a CpG position within such a sample, a person skilled in the art may use a quantitative assay for determining the methylation level (e.g., percent, fraction, ratio, proportion or degree) at a particular CpG position other than a methylation status. Accordingly, the term methylation state or methylation status should also be taken as a value reflecting the methylation level at a CpG position. Unless specifically stated, the term "hypermethylated" or "upmethylated" shall be taken as a methylation level above a specified critical value, wherein the critical value may be a value representing the average or median methylation level for a given population, or is preferably an optimized critical level. The "critical value" is also referred herein as a "threshold value". In the context of the present invention, the term "methylated", "hypermethylated" or "upmethylated" shall be taken to include a methylation level above the critical value zero (0) % (or an equivalent thereof) for all CpG positions within and associated with (e.g. in a promoter or a regulatory region) the genes or genomic sequence selected from the group consisting of the above Septin 9 and RNF180 gene sequences.

In certain embodiments, the method of the present application specifically comprises: contacting Septin9 and RNF180 genes or fragments thereof treated by the reagent with an amplification enzyme and primers such that the treated genes or fragments are amplified to produce amplification products or not amplified; detecting the amplification products with probes; and determining the methylation level of at least one CpG dinucleotide of the DNA sequences of Septin9 and RNF180 genes based on the presence or absence of the amplification products.

Also, the contact or amplification typically comprises applying at least one method selected from the group consisting of: use of a thermostable DNA polymerase as the amplification enzyme; use of a polymerase lacking 5'-3' exonuclease activity; use of a polymerase chain reaction (PCR); and generation of a nucleic acid molecule with an amplification product with a detectable label.

That is, the methylation level is preferably determined by a PCR method, and methods such as "fluorescence-based real-time PCR technique" (Eads et al., Cancer Res. 59: 2302-2306, 1999), Ms-SNuPE™ (Methylation-sensitive Single Nucleotide Primer Extension) reaction (Gonzalgo & Jones, Nucleic Acids Res. 25: 2529-2531, 1997), methylation-specific PCR ("MSP"; Herman et al., Proc. Natl. Acad. Sci. USA 93: 9821-9826, 1996; U.S. Pat. No. 5,786,146), and methylated CpG island amplification ("MCA"; Toyota et al., Cancer Res. 59: 2307-12, 1999) are used to detect the methylation level of at least one CpG dinucleotide of the DNA sequences of Septin9 and RNF180 gene.

Among these, "fluorescence-based real-time PCR" is a high-throughput quantitative methylation assay that utilizes fluorescence-based real-time PCR (TaqMan) technology, and requires no further manipulations after the PCR step (Eads et al., Cancer Res. 59: 2302-2306, 1999). Briefly, "fluorescence-based real-time PCR" process begins with a mixed sample of genomic DNA that is converted, in a sodium bisulfite reaction, to a mixed pool of methylation-dependent sequence differences according to the standard procedures (the bisulfite process converts unmethylated cytosine residues to uracil). Fluorescence-based PCR is then performed in a "biased" (with the PCR primers that overlap known CpG dinucleotides) reaction. Sequence discrimination can occur both at the level of the amplification process and at the level of the fluorescence detection process.

"Fluorescence-based real-time PCR" assay may be used as a quantitative test for methylation pattern in a genomic DNA sample, wherein sequence discrimination occurs at the level of probe hybridization. In this quantitative manner, the PCR reaction provides for a methylation specific amplification in the presence of a fluorescent probe that overlaps a particular putative methylation site. An unbiased control for the amount of input DNA is provided by a reaction in which neither the primers, nor the probes overlie any CpG dinucleotides. "Fluorescence-based real-time PCR" method can be used with any suitable probes, such as "TaqMan_", "Lightcycler_", etc.

TaqMan_probe is dual-labeled with fluorescent "reporter" and "quencher" molecules, and is designed to be specific for a region having a relatively high GC content so that it melts out in the PCR cycle at an about 10° C. higher temperature than the forward or reverse primer. This allows TaqMan_probe to remain fully hybridized during the PCR annealing/extension step. As a Taq polymerase enzymatically synthesizes a new strand during PCR, it will eventually reach the annealed TaqMan_probe. The Taq polymerase 5' to 3' endonuclease activity will then displace the TaqMan_probe by digesting it to release the fluorescent reporter molecule for quantitative detection of its now unquenched signal using a real-time fluorescent detection system.

A typical reagent (e.g., can be found in a kit based on"fluorescence-based real-time PCR") for "fluorescence-based real-time PCR" assay may include, but are not limited to: PCR primers for a particular gene (or DNA sequence or CpG island treated by bisulfite); TaqMan_or Lightcycler_probes; optimized PCR buffers and deoxynucleotides; and a Taq polymerase.

However, specifically, in a preferred embodiment, the method comprises the following steps:

In a first step, a tissue sample to be analyzed is obtained. The source may be any suitable sources, such as cell lines, histological sections, tissue biopsies, paraffin-embedded tissues, body fluids, stool, colonic effluent, urine, plasma, serum, whole blood, isolated blood cells, cells isolated from blood, and any possible combination thereof. Preferably, the source of DNA is stool or body fluids selected from the group consisting of colonic effluent, urine, plasma, serum, whole blood, isolated blood cells, and cells isolated from blood.

Genomic DNA is then isolated from the sample by any standard means in the prior art, including use of a commercially available kit. Briefly, where the DNA of interest is encapsulated in cellular membrane, the biological sample must be disrupted and lysed by enzymatic, chemical or mechanical means. Then proteins and other contaminants can be removed e.g., by digestion with proteinase K. The genomic DNA is then recovered from the solution. This may be carried out by means of a variety of methods including salting out, organic extraction, or binding of the DNA to a solid phase support. The choice of method will be affected by several factors including time, expense and quantity of DNA as required.

When the sample DNA is not enclosed in cell membrane (e.g. circulating DNA from a blood sample), the standard methods in the art for isolation and/or purification of DNA may be employed. Such methods include use of a protein degenerating reagent, e.g., chaotropic salt, such as guanidine hydrochloride or urea; or a detergent, e.g. sodium dodecyl sulphate (SDS), cyanogen bromide. Alternative methods include, but are not limited to, ethanol precipitation or propanol precipitation, vacuum concentration by means of centrifuge amongst others. A person skilled in the art may also make use of devices, such as filter devices, e.g., ultrafiltration, silica surfaces or membranes, magnetic particles, polystyrol particles, polystyrol surfaces, positively charged surfaces, and positively charged membranes, charged membranes, charged surfaces, charged switch membranes, charged switch surfaces.

Once the nucleic acids have been extracted, the genomic double stranded DNA is used in the analysis.

In the second step of the method, the genomic DNA sample is treated in such a manner that 5'-unmethylated cytosine base is converted to uracil, thymine, or another base which is different from cytosine in terms of hybridization behaviour. This will be understood as "pre-treatmen" or "treatment" herein.

This is preferably achieved by means of treatment with a bisulfite reagent. The term "bisulfite reagent" refers to a reagent including bisulfite, disulfite, hydrogen sulfite, or combination thereof, which is useful as disclosed herein to distinguish between methylated and unmethylated CpG dinucleotide sequences. The treatment is known in the art (e.g., PCT/EP2004/011715, which is incorporated by reference in its entirety). It is preferred that the bisulfite treatment is conducted in the presence of a denaturing solvent, such as but not limited to, n-alkylene glycol, particularly diethylene glycol dimethyl ether (DME), or in the presence of dioxane or dioxane derivatives. In a preferred embodiment, the denaturing solvent is used in a concentration between 1% and 35% (v/v). It is also preferred that the bisulfite reaction is carried out in the presence of a scavenger, such as but not limited to, a chromane derivative, e.g., 6-hydroxy-2,5,7,8-tetramethylchromane 2-carboxylic acid or trihydroxybenzoic acid, and derivates thereof, e.g., gallic acid (see PCT/EP2004/011715, which is incorporated by reference in its entirety). The bisulfite conversion is preferably carried out at a reaction temperature between 30° C. and 70° C., whereby the temperature is increased to over 85° C. in a short period of time during the reaction (see PCT/EP2004/011715, which is incorporated by reference in its entirety). The bisulfite treated DNA is preferably purified prior to the quantification. This may be conducted by any means known in the art, such as but not limited to, ultrafiltration, preferably carried out by means of Microcon$^{\lambda\text{-TM}}$ column (manufactured by Millipor$^{\lambda\text{-TM}}$).

In the third step of the method, the fragments of the treated DNA are amplified using the primer oligonucleotides according to the present invention and an amplification enzyme. The amplification of several DNA fragments can be carried out simultaneously in one same reaction vessel. Typically, the amplification reaction is carried out by a polymerase chain reaction (PCR). Preferably, the amplification products are 100 to 2,000 base pairs in length.

The methylation of Septin9 gene or fragment thereof is detected by e.g. the following primers and probe for Septin9:
Primer: SEQ ID No: 14 GTAGTAGTTAGTTTAGTATT-TATTTT
Primer: SEQ ID No: 14 CCCACCAACCATCATAT
Primer: SEQ ID No: 14 GAACCCCGCGATCAACGCG The methylation of RNF180 gene or fragment thereof is detected by the primers and probes for RNF180 screened by the above-described screening methods. For example, in a preferred embodiment, any one of combinations 1, 2, 3 and 4 of primers and probes described above can be used.

The fragments obtained by the amplification can carry a label which is directly or indirectly detectable. Preferably, the label is in the form of a fluorescence label, a radionuclide, or an attachable molecule fragment.

In the fourth step of the method, the amplification products obtained in the third step of the method are analysed in order to determine the methylation status of the CpG dinucleotides prior to the treatment.

In the fourth step, the detection of the amplification products is conducted with probes for a real-time detection. In the present invention, the real-time PCR detection can be performed on a variety of commercial real-time PCR apparatus according to the standard operations in the prior art. The real-time PCR detection is performed on a Life Technologies instrument (7500Fast) according to certain specific embodiments. The PCR reaction mixture consists of the bisulfite-converted DNA templates 25-40 ng and 300-600 nM primers, 150-300 nM probes, 1UTaq polymerase, 50-400 uM each dNTPs, 1 to 10 mM MgCl2 and 2×PCR buffer with a final volume of 2 ul to 100 ul, which is kept at 85 to 99° C. for 3-60 minutes to amplify samples in pre-cycling, followed by 35 to 55 cycles of annealing at 50 to 72° C. for 1 to 30 seconds, annealing at 45 to 80° C. for 5 to 90 seconds, and denaturing at 85 to 99° C. for 5 to 90 seconds.

Only by the amplification observed on the methylated RNF180 gene and Septin9 gene fragments, the gene fragments are detected with the probes specific for the RNF180 and Septin9 promoter regions contained 5-methylcytosine. Furthermore, in certain specific embodiments, β-actin is used as an internal reference in PCR, the β-actin amplicon is created by using the primers complementary to the β-actin sequence, and the β-actin amplicon is detected with the particular probes. Each sample is subjected to at least one real-time PCR, and in some embodiments, two detections based on real-time PCR are performed.

In the fifth step of the method, the methylation status of at least one CpG dinucleotide in the DNA sequence of Septin9 and RNF180 genes are presented respectively, which is determined by the cycle threshold Ct value of the polymerase chain reaction, and then the following steps are further included: A) comparing the Ct values of PCR corresponding to Septin9 in the tested sample to the predetermined cut value (i.e., the critical Ct value) of Septin9 to determine whether the analysis result based on Septin9 gene is positive; B) comparing Ct values of PCR corresponding to RNF180 in the tested sample to a predetermined cut value of RNF180 to determine whether the analysis result based on the RNF180 gene represents normal, gastritis or gastric cancer (positive); C) combining the results of steps A) and B) to determine whether the final analysis result of the sample represents normal, gastritis, or gastric cancer (positive).

According to the specific embodiments of the present application, the critical Ct values for gastric cancer, gastritis, and normal with respect to Septin9 and RNF180 are determined based on the mean Ct values of Septin9 and RNF180 of a number of gastric cancer samples and normal samples. In certain preferred embodiments, the kit for measuring the methylation status of at least one CpG dinucleotide of the DNA sequence of Septin9 gene was purchased from Epigenomics AG (Germany), so that critical Ct value of Septin 9 can be determined as 45 according to the instructions of Epigenomics AG. And the critical Ct value of RNF180 is determined based on the mean Ct value of RNF180 in a certain number of gastric cancer, gastritis and normal samples. And the critical Ct value of RNF180 is also related to the actual sensitivity as required, and the higher the sensitivity requirement is, the greater the selected critical Ct value is.

Furthermore, the present application allows the analysis of Ct value using different methodologies. For example, ΔCt or dCT is used, and the Ct of actin is takes as the internal control of the PCR, and the dCT value of Septin 9 is obtained by substracting the Ct of actin from the Ct of Septin 9. Similarly, the dCT value of RNF 180 is obtained by substracting the Ct of actin from the Ct of RNF 180. Accordingly, if ΔCt or dCT is used as the detection standard, in the fifth step of the method, the methylation status of at least one CpG dinucleotide within the DNA sequences of Septin9 and RNF180 genes is presented respectively, which is determined by the cycle threshold Ct value of the polymerase chain reaction, and then the following steps are further included: A) comparing the ΔCt values of PCR corresponding to Septin9 in the tested sample to the predetermined Δcut value (i.e., the critical Ct value) of Septin9 to determine whether the analysis result based on Septin9 gene is positive; B) comparing the ΔCt values of PCR corresponding to RNF180 in the tested sample to the predetermined Δcut value of RNF180 to determine whether the analysis result based on RNF180 gene represents normal, gastritis or gastric cancer (positive); C) combing the results of steps A) and B) to determine whether the final analysis result of the samples represents normal, gastritis or gastric cancer (positive).

In summary, the present application improves the sensitivity and specificity of cancer detection, especially those of gastric cancer detection, by the above-described composition, nucleic acid sequences, kit, use thereof, and above-described detection method, which combine the nucleic acid sequences for detecting the methylation of Septin9 and RNF180 genes or fragments thereof respectively, and thus ensures the accuracy and reliability of the detection results; and has achieved grading of gastritis and gastric cancer by combining the two biomarkers Septin9 and RNF180, so that both the sensitivity and specificity of disease grading are improved.

The specific examples will be described in detail below.

EXAMPLES

Example 1: Screening of Primers and Probes

According to certain specific embodiments, the kit for measuring the methylation status of at least one CpG dinucleotide of the DNA sequence of Septin9 gene was purchased from Epigenomics AG (Germany). Therefore, the primers and probes for the experiment for Septin9 gene were obtained directly according to the instructions of the kit. For RNF180 gene, multiple sets of combinations of probes and primers can be designed, and each combination of the probes and primers may be different in the performance. The probes and primers were screened in the following examples.

In this example, the primers and probes for RNF180 were first screened with an artificially methylated template and an unmethylated template. The example includes the following steps:

First, various primers and probes for RNF180 were designed, provided that they are capable of being equivalent to, complementary to, or hybridize under moderately stringent or stringent conditions to at least 15 nucleotides selected from the group consisting of SEQ ID Nos: 10 to 12, or complementary sequence thereof.

The PCR amplifications were then carried out with the different combinations of probes and primers using an artificially methylated oligonucleotide sequence and an artificially unmethylated oligonucleotide sequence as templates. The conditions for the PCR amplifications employed in the experiment were as follows: the real-time PCR was performed on a Life Technologies instrument (7500Fast). The PCR reaction mixture consisted of 35 ng bisulfite-converted DNA templates and 450 nM primers, 225 nM probes, 1UTaq polymerases, 200 um each dNTPs, 4.5 mM MgCl2 and 2×PCR buffer with a final volume of 30 ul, which was kept at 94° C. for 20 minutes to amplify samples in precycling, followed by 45 cycles of annealing at 62° C. for 5 seconds, annealing at 55.5° C. for 35 seconds, and denaturing at 93° C. for 30 seconds.

Finally, the four sets of suitable primers and probes were screened based on the PCR experiment results:

Primers and probes combination 1 (amplicon 66 bp, −43 bp to +23b from the transcription initiation site)

```
(180F7)
                                          SEQ ID No: 1
5'-GTTCGAGGTCGCGGGGTC-3'

(180P7)
                                          SEQ ID No: 2
5'-CAL Fluor Red-

AACGCTCGAACTATACCTACAACCCC-BHQ2-3'

(180R7)
                                          SEQ ID No: 3
5'-ACAAAAACCAAACCCCGCG-3'
```

Primers and probes combination 2 (amplicon 86 bp, +5 bp to +91 bp with respect to the transcription initiation site)

```
(180F24)
                                          SEQ ID No: 4
5'-GCGGGGTTTGGTTTTTGT-3'

(180P2)
                                          SEQ ID No: 5
5'-CAL Fluor Red-CCGACGACGACGATACCG-BHQ2-

3'

(180R2)
                                          SEQ ID No: 6
5'-ACAACCAAACTCTAAAAACTCG-3'
```

Primers and probes combination 3 (amplicon 130 bp, +5 bp to +135 bp with respect to the transcription initiation site)

```
(180F24)
                                          SEQ ID No: 4
5'-GCGGGGTTTGGTTTTTGT-3'

(180P14)
                                          SEQ ID No: 7
5'-CAL Fluor Red-CGTCGGAGTCGTAGCGAGTTT-BHQ2-

3'

(180R135)
                                          SEQ ID No: 8
5'-AAAACCTCCAACTTCACACCC-3'
```

Primers and probes combination 4 (amplicon 91 bp, +5 bp to +96 bp with respect to the transcription initiation site)

(180F24)
SEQ ID No: 4
5'-GCGGGGTTTGGTTTTTGT-3'

(180P14)
SEQ ID No: 7
5'-CAL Fluor Red-CGTCGGAGTCGTAGCGAGTTT-BHQ2-3'

(180R14)
SEQ ID No: 9
5'-CGCCAACAACCAAACTCTAA-3'

Conclusion: there was amplification based on the artificially methylated oligonucleotide template and no amplification based on the artificially unmethylated oligonucleotide template, and it indicates that the primers and probes are designed correctly. The four sets of primers and probes are capable of distinguishing the methylated template from the unmethylated template, all of which could be used as the primers and probes in the experiment for RNF180. Although the effects of the different combinations of probes and primers are different, all the above four sets of probes are suitable as the primers and probes in the experiment for RNF180.

Next, the primers and probes for RNF180 were further screened with cancer and normal DNA as templates.

The samples were obtained from 4 cases of gastric cancer (S1-S4), 2 cases of colon cancer (C1-C2), 2 cases of lung cancer (L1-L2), 1 case of blood cancer (Jurkat) and 1 case of normal people (WBC). The Genomic DNAs were extracted from 4 cases of gastric cancer, 2 cases of colon cancer, 2 cases of lung cancer, 1 case of blood cancer and 1 case of normal people. The genomic DNA of Jurkat cells was used as a positive control, and normal DNA as a negative control. All cancer samples were obtained from BIOCHAIN INC. The normal people sample was obtained from BioReclamation IVT Inc. The extraction of DNA can be carried out using any standard means in the prior art, and in particular, in this example, all the DNAs of human samples were extracted by the EPi proColon Plasma Quick Kit of Epigenomics AG.

The genomic DNA sample was then pretreated such that 5'-unmethylated cytosine base was converted to uracil, thymine, or another base which is different from cytosine in terms of hybridization behaviour. In the example, this pre-treatment was achieved by treatment with a bisulfite reagent. The DNA modification with bisulfite was carried out by the EPi proColon Plasma Quick Kit.

Next, the four sets of primers and probes for RNF180 described above were added to the pre-treated genomic DNA samples of 4 cases of gastric cancer, 2 cases of colon cancer, 2 cases of lung cancer, 1 case of blood cancer and 1 case of normal person to carry out 4 groups of PCR experiments for RNF 180, and the primers and probes for Septin9 were added for multiple detection of the PCR experiments for RNF180 and Septin9. The PCR reagents for Septin9 were purchased from Epigenomics AG. The Real-time PCR was performed with the bisulfite-converted DNAs.

The PCR amplification conditions employed in the experiment were as follows: the real-time PCR detection was performed on a Life Technologies instrument (7500Fast). The PCR reaction mixture consisted of the bisulfite-converted DNA templates 35 ng and 450 nM primers, 225 nM probes, 1UTaq polymerases, 200 um each dNTPs, 4.5 mM MgCl2 and 2×PCR buffer with a final volume of 30 ul, which was kept at 94° C. for 20 minutes to amplify samples in precycling, followed by 45 cycles of annealing at 62° C. for 5 seconds, annealing at 55.5° C. for 35 seconds, and denaturing at 93° C. for 30 seconds.

Finally, the Ct values of real-time PCR for RNF180 gene in the genomic DNA samples of 4 cases of gastric cancer, 2 cases of colon cancer, 2 cases of lung cancer, 1 case of blood cancer and 1 case of normal person were determined, and the Ct values of real-time PCR for Setptin9 gene in the genomic DNA samples of 4 cases of gastric cancer, 2 cases of colon cancer, 2 cases of lung cancer, 1 case of blood cancer and 1 case of normal people were determined (as shown in FIG. 1).

FIG. 1 shows that in the multiple detection of the methylated DNAs of Septin9 and RNF180, none of the four sets of primers and probes for RNF180 affects the detection of Septin9. The abscissa SC_set 1-4 represents the sets of primers and probes 1-4, the bars in each set represent S1, S2, S3, S4, C1, C2, L1, L2, Jurkat and WBC from left to right respectively, and the ordinate is the Ct value of Septin9, wherein S1-S4 represent 4 cases of gastric cancer, C1-C2 represent 2 cases of colon cancer, L1-L2 represent 2 cases of lung cancer, Jurkat represents 1 case of blood cancer (positive control), and WBC represents 1 case of normal people (negative control).

It can be seen from the Ct value of the real-time PCR for RNF180 gene that the amplification of RNF180 is high in cancerous DNA, and low in normal DNA. The specificity of primers and probes for RNF180 can distinguish from cancerous DNA and normal DNA. The different combinations of primers and probes for RNF180 achieve different effect. The amplification of RNF180 is very high in the DNA of blood cancer Jurkat cells.

As shown in FIG. 1, it can be seen from the Ct value of the real-time PCR of Setptin9 gene that the primers and probes for RNF180 do not affect the detection of Septin9 in the multiple detection. The primers and probes for Septin9 can distinguish from cancerous DNA and normal DNA, without being affected by RNF180. The different combinations of primers and probes for RNF180 do not affect the detection of Septin9. There is very high amplification of RNF180, but no amplification of Septin9 in the DNA of blood cancer Jurkat cells. The methylation of RNF180 and Septin9 is similar in some cancers, but different in others.

According to the above example, all of the four sets of probes and primers for RNF180 designed by the present application can distinguish cancerous DNA from normal DNA. Further, in the following examples, the above-mentioned probes and primers were used to further compare and analyze the methylation level of the DNA in the biological samples of normal people, patients with gastritis, and patients with gastric cancer. In particular, in order to enable the grading of disease severity using the result of a real-time PCR, a critical value of Ct, i.e. a cut value of a real-time PCR, is first determined by analyzing a certain amount of samples, and the cut value serves to grade disease severity according to the different requirements on sensitivities and specificities. In the following examples, the corresponding Ct values which refelct the levels of methylated DNA of Septin9 and RNF180 were determined in the biological samples of the patients with gastric cancer, patients with gastritis, and normal people, thereby providing a judgmental critical value, i.e. the critical cut value, for grading disease severity (gastric cancer, gastritis, and normal).

Example 2: Preliminary Clinical Results of Multiple Detection of Methylated DNA of RNF180 and Septin9 in Plasma from Patients with Gastric Cancer The samples were obtained from 10 patients with gastric cancer and 11 healthy people. The Genomic DNAs were extracted from the 10 patients with gastric cancer and 11 healthy people. All the cancer samples were obtained from BIOCHAIN Inc. The normal people sample was obtained from BioReclamation IVT Inc. The extraction of DNA can be carried out using any standard means in the prior art, and in particular, in this example, the DNAs of all samples were extracted by the EPi proColon Plasma Quick Kit of Epigenomics AG.

The genomic DNA samples were then pretreated such that 5'-unmethylated cytosine base was converted to uracil, thymine, or another base which is different from cytosine in terms of hybridization behaviour. In the example, this pretreatment was achieved by treatment with a bisulfite reagent. The DNA modification with bisulfite was carried out by the EPi proColon Plasma Quick Kit.

Next, the second set of primers and probes for RNF180 described above was added to the pre-treated genomic DNA samples of 10 patients with gastric cancer and 11 healthy people to carry out the PCR experiment for RNF 180, and the primers and probes for Septin9 were added for multiple detection of the PCR experiments for RNF180 and Septin9. The PCR reagents for Septin9 were purchased from Epigenomics AG. The Real-time PCR was performed with the bisulfite-converted DNAs.

The PCR amplification conditions employed in the experiment were as follows: the real-time PCR was performed on a Life Technologies instrument (7500Fast). The PCR reaction mixture consisted of the bisulfite-converted DNA templates 35 ng and 450 nM primers, 225 nM probes, 1UTaq polymerases, 200 um each dNTPs, 4.5 mM MgCl2 and 2×PCR buffer with a final volume of 30 ul, which was kept at 94° C. for 20 minutes to amplify samples in precycling, followed by 45 cycles of annealing at 62° C. for 5 seconds, annealing at 55.5° C. for 35 seconds, denaturing at 93° C. for 30 seconds.

Finally, the Ct values of real-time PCR for RNF180 gene in the genomic DNA samples from 10 patients with gastric cancer and 11 healthy people were determined, and the Ct values of real-time PCR for Setptin9 gene in the genomic DNA samples from 10 patients with gastric cancer and 11 healthy people were determined respectively, as shown in the following table 1-3.

TABLE 1 multiple detection of methylated DNA of Septin9 and RNF180 in 10 patients with gastric cancer

| Cancer samples | Ct RNF180 | Ct Septin9 | Correlation | Diagnosis |
| --- | --- | --- | --- | --- |
| 6/Asian/male/63 | / | 38.19 | complementary | Positive |
| 35/Asian/male/58 | 37.62 | / | complementary | Positive |
| 36/Asian/female/53 | 34.46 | 38.34 | | Positive |
| 39/Asian/female/58 | 31.84 | 34.51 | | Positive |
| 41/Asian/male/53 | 33.28 | 38.67 | | Positive |
| 42/Asian/female/58 | 36.96 | / | complementary | Positive |
| 43/Asian/female/56 | 32.90 | 36.03 | | Positive |
| 59/Asian/male/57 | 34.56 | 38.00 | | Positive |
| 61/Asian/male/69 | 34.71 | / | complementary | Positive |
| 68/Asian/female/49 | 35.15 | No Ct | complementary | positive |
| Positive rate | 90% | 70% | | Positive |

TABLE 2 multi-detection of methylated DNA of Septin9 and RNF180 in 6 healthy people

| Plasma from healthy people | Ct RNF180 | Ct Septin9 |
| --- | --- | --- |
| H1/Asian/male/30 | / | / |
| H2/Asian/female/27 | 36.45 | / |
| H3/Asian/male/24 | / | / |
| H4/Asian/female/45 | / | / |
| H5/Asian/male/35 | / | / |
| H6/Asian/male and female/32 | / | / |
| Specificity | 83% | 100% |

TABLE 3 multi-detection of methylated DNA of Septin9 and RNF180 in 5 healthy people

| | RNF180 | | Septin9 | |
| --- | --- | --- | --- | --- |
| Sample | Ct mean value | Ct SD | Ct mean value | Ct SD |
| #1: Spain/male/30 | / | / | / | / |
| #2: Black/male/34 | / | / | / | / |
| #3: Black/female/19 | / | / | / | / |
| #4: Black/female/31 | / | / | / | / |
| #5: Black/female/42 | / | / | / | / |
| RC1 | 28.65 | 0.01 | 38.14 | 0.60 |
| RC2 | 28.42 | 0.01 | 38.46 | 1.71 |
| Gastric cancer #3 | 29.93 | 0.03 | 29.86 | 0.15 |
| Water | / | / | / | / |

Both RC1 and RC2 are the references. A Ct value of 45 is taken as a critical value for the PCR of RNF180 and Septin9, and the Ct value above 45 represents normal, and the Ct value below 45 represents positive for cancer. "/" indicates the Ct value is above 45.

In the multiple detection of the methylated DNA of Septin9 and RNF180, the Ct value below 45 represents positive for gastric cancer. The positive results of the detection of methylated DNA of Septin9 and RNF180 are combined, and complementary to each other. 10 patients with gastric cancer are diagnosed as positive. The sensitivity of gastric cancer reaches 100%. In 11 healthy people, 10 are diagnosed as negative and the specificity reaches 91%.

Figure 2:
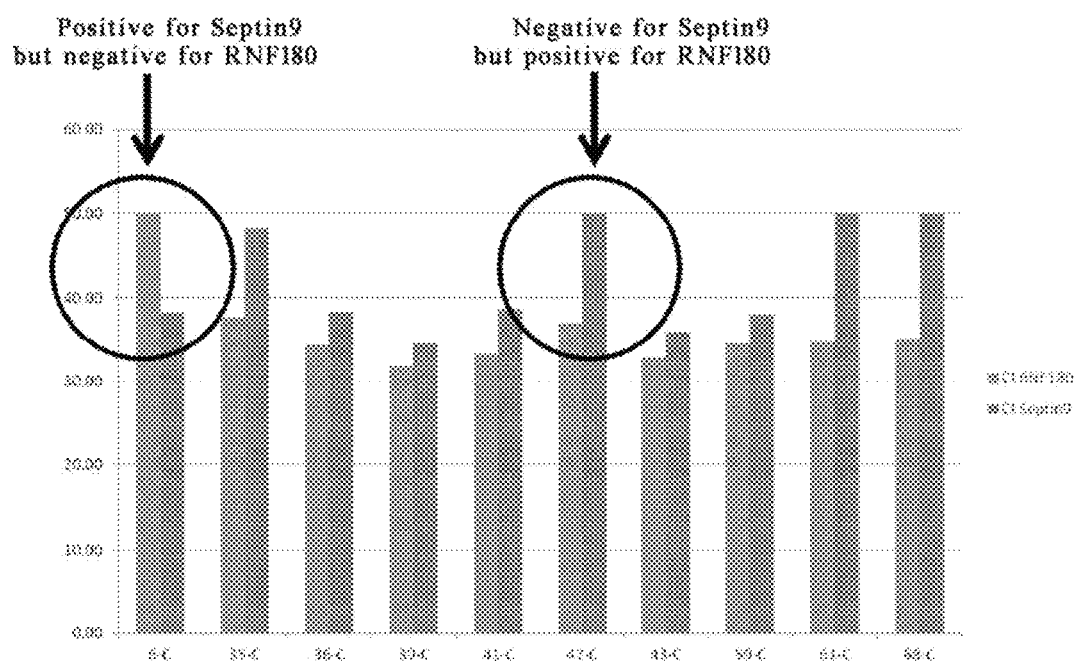
FIG. 2 shows that the positive results of multiple detection of gastric cancer based on the methylated DNAs of Septin9 and RNF180 are complementary.

The Ct values of PCR of RNF180 and Septin9 in 10 gastric cancer patients in Table 1 are shown in the form of a histogram, as shown in FIG. 2. The abscissa in FIG. 2 is 10 cases of gastric cancer and the ordinate is the Ct values of Septin9 and RNF180.

The positive results of methylated DNA detection of Septin9 and RNF180 are combined, that is, the positive results of methylated DNA detection of Septin9 and RNF180 are complementary to each other, and the sensitivity of gastric cancer reaches 100%. The positive results of Septin9 and RNF180 are complementary in the diagnosis of gastric cancer.

Example 3: Grading of Gastric Cancer, Gastritis, and Normal People by Multiple Detection of Methylated DNA of RNF180 and Septin9

The example comprises the following steps:

First, the plasma was obtained from 42 patients with gastric cancer, 14 patients with gastritis, and 11 normal people. The Genomic DNAs were extracted from from the patients with gastric cancer, patients with gastritis, and normal people. All the cancer samples were obtained from BIOCHAIN Inc. The normal people samples were obtained from BioReclamation IVT Inc. The Extraction of DNA can be carried out using any standard means in the prior art, and in particular, in this example, the DNAs of all samples were extracted by the EPi proColon Plasma Quick Kit of Epigenomics AG.

The genomic DNA samples were then pretreated such that 5'-unmethylated cytosine base was converted to uracil, thymine, or another base which is different from cytosine in terms of hybridization behaviour. In the example, this pretreatment was achieved by treatment with a bisulfite reagent. The DNA modification with bisulfite was carried out by the EPi proColon Plasma Quick Kit.

Next, the second set of primers and probes for RNF180 described above were added to the pre-treated genomic DNA samples of 42 patients with gastric cancer, 14 patients with gastritis, and 11 normal people to carry out the PCR experiments for RNF 180, and the primers and probes for Septin9 were added for multiple detection of the PCR experiments for RNF180 and Septin9. The PCR reagents for Septin9 were purchased from Epigenomics AG. The Real-time PCR was performed with the bisulfite-converted DNAs.

The PCR amplification conditions employed in the experiments were as follows: the real-time PCR detection was performed on a Life Technologies instrument (7500Fast). The PCR reaction mixture consisted of the bisulfite-converted DNA templates 35 ng and 450 nM primers, 225 nM probes, 1UTaq polymerases, 200 um each dNTPs, 4.5 mM MgCl2 and 2×PCR buffer with a final volume of 30 ul, which was kept at 94° C. for 20 minutes to amplify samples in precycling, followed by 45 cycles of annealing at 62° C. for 5 seconds, annealing at 55.5° C. for 35 seconds, denaturing at 93° C. for 30 seconds.

Figure 3:
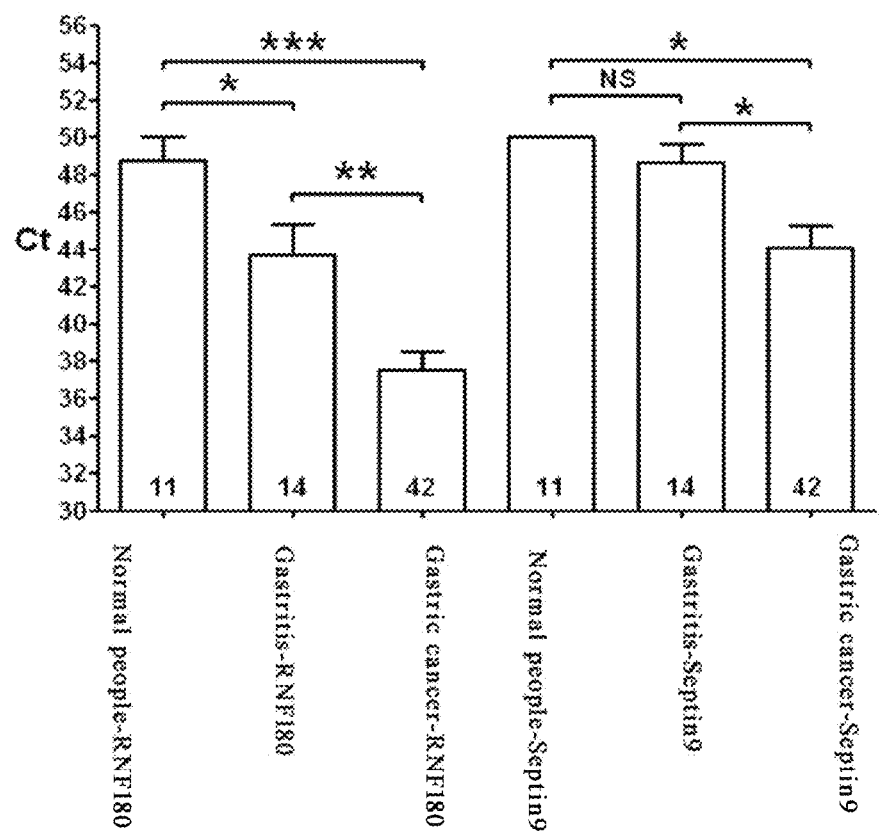
FIG. 3 shows a histogram of the average Ct values of multiple detection of gastric cancer, gastritis, and normal people based on the methylated DNAs of Septin9 and RNF180.
Figure 4:
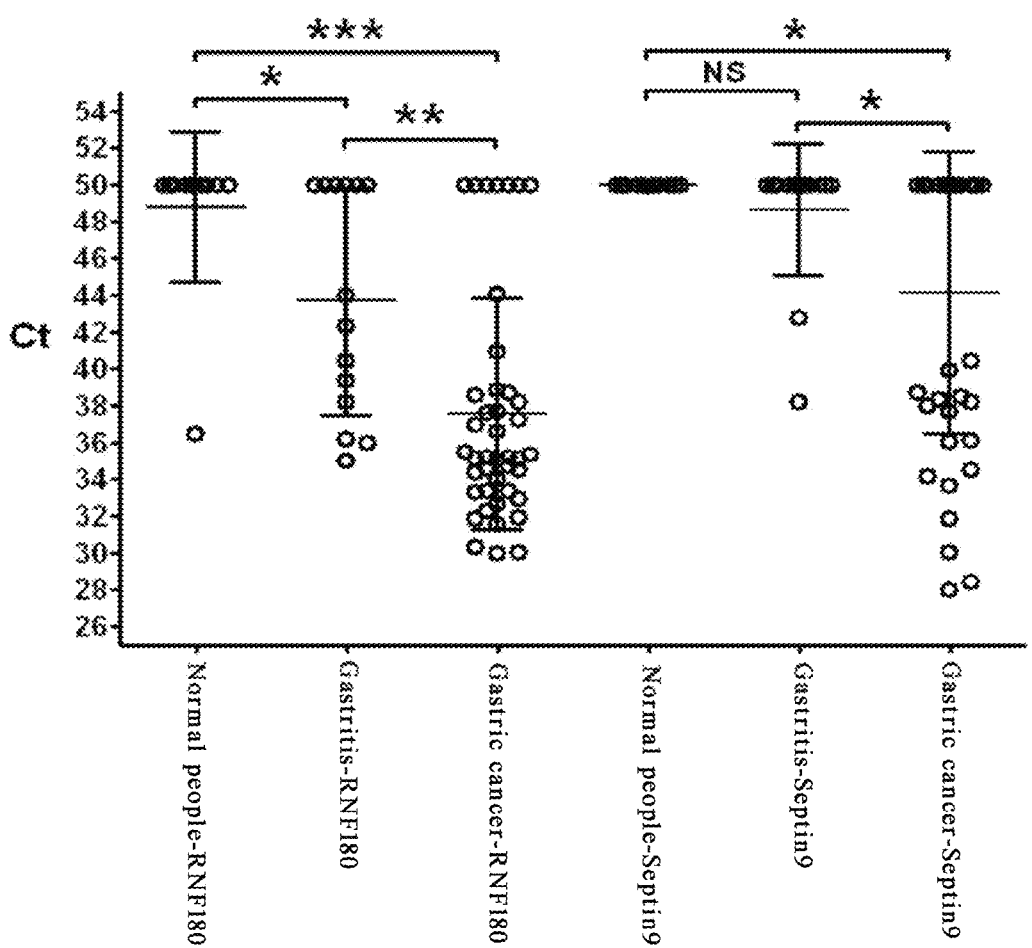
FIG. 4 shows a scatter diagram of the Ct values of multiple detection of gastric cancer, gastritis, and normal people based on the methylated DNAs of Septin9 and RNF180.

Finally, the Ct values of real-time PCR for RNF180 gene in the genomic DNA samples of 42 patients with gastric cancer, 14 patients with gastritis, and 11 normal people were determined, and the Ct values of real-time PCR for Setptin9 gene in the genomic DNA samples of 42 patients with gastric cancer, 14 patients with gastritis, and 11 normal people were determined, respectively. And a statistical analysis was performed according to the determined Ct values. FIGS. 3 and 4 are the histogram and scatter diagram of the mean Ct values of multiple detection of methylated DNA of Septin9 and RNF180 in gastric cancer, gastritis, and normal people. The abscissa represents from the left to the right the mean Ct values of the methylation level of RNF180 gene in 11 normal people, the mean Ct values of the methylation level of RNF180 gene in 14 patients with gastritis, the mean Ct values of methylation level of RNF180 gene in 42 patients with gastric cancer, the mean Ct values of methylation level of Setptin9 gene in 11 normal people, the mean Ct values of methylation level of Setptin9 gene in 14 patients with gastritis, and the mean Ct values of methylation level of Setptin9 gene in 42 patients with gastric cancer, respectively. * represents a significant difference,  represents a very significant difference, and * represents an extremely significant difference.

It can be seen from the above figures that in the detection of RNF180, there is a very significant difference of Ct values between gastric cancer and gastritis, a significant difference between normal people and gastritis, and an extremely significant difference between normal people and gastric cancer, thus providing a critical value for judgement, i.e. the cut value for grading disease severity (gastric cancer, gastritis, and normal). It also indicates that the disease severity can be graded by the detection result of methylation of RNF180, for example, gastric cancer, gastritis, and normal people can be graded. In the detection of Septin9, there is a significant difference of Ct value between gastric cancer and gastritis, and a significant difference between normal people and gastric cancer.

In this example, the sensitivity of the gastric cancer detection is 83.3%, the sensitivity of the gastritis detection is 64.3%, and the specificity of completely normal is 90.9% when the Ct value of 45 is taken as the critical value for Septin9 and the Ct value of 45 is taken as the critical value for RNF180. The sensitivity of gastric cancer is 78.6%, the sensitivity of gastritis is 28.3%, and the specificity of completely normal is 90.9% when the Ct value of 45 is taken as the critical value for Septin9, a Ct value of RNF180 below 39 presents gastric cancer, and a Ct value of RNF180 of 39-45 presents gastritis.

The above experimental results indicate that disease severity can be graded by the multiple detection of methylated DNA of RNF180 and Septin9 of the present invention, for example, gastric cancer, gastritis, and normal people can be graded.

Example 4: Grading of Normal People, Superficial, Atrophic Gastritis/Gastritis with Intestinal Metaplasia, Gastric Cancer Stages I, II, III and IV Based on Multiple Detection of Methylated DNA of RNF180 and Septin9 (RS19)

The samples were obtained from 15 normal people, 31 cases of superficial gastritis, 6 cases of atrophic gastritis/gastritis with intestinal metaplasia, 19 cases of gastric cancer stage I, 20 cases of gastric cancer stage II, 22 cases of gastric cancer stage III and 10 cases of gastric cancer stage IV. The Genomic DNA was extracted from each sample. The Extraction of DNA can be carried out with any standard means known in the prior art, and particularly, in this example, the DNAs of all samples were extracted by the EPi proColon Plasma Quick Kit of Epigenomics AG.

The genomic DNA samples were then pretreated such that 5'-unmethylated cytosine base was converted to uracil, thymine, or another base which is different from cytosine in terms of hybridization behaviour. In the example, the pretreatment was achieved by a bisulfite reagent. The DNA modification with the bisulfite was carried out by the EPi proColon Plasma Quick Kit.

Next, the second set of primers and probes for RNF180 described above were added to the pre-treated genomic DNA samples of 15 normal people, 31 cases of superficial gastritis, 6 cases of atrophic gastritis/gastritis with intestinal metaplasia, 19 cases of gastric cancer stage I, 20 cases of gastric cancer stage II, 22 cases of gastric cancer stage III and 10 cases of gastric cancer stage IV so as to carry out the PCR experiment for RNF 180, and the primers and probes for Septin9 and β-actin were added for the multiple detection of the PCR experiments for RNF180, Septin9 and β-actin. The PCR reagents for Septin9 and β-actin were purchased from Epigenomics AG. The Real-time PCR was performed with the DNAs converted by the bisulfite.

Wherein the PCR amplification conditions employed in the experiment were as follows: the real-time PCR detection was performed on a Life Technologies instrument (7500Fast). The PCR reaction mixture consisted of 35 ng DNA templates converted by the bisulfite and 450 nM primers, 225 nM probes, 1UTaq polymerases, 200 um each dNTPs, 4.5 mM MgCl2 and 2×PCR buffer with a final volume of 30 ul, which was kept at 94° C. for 20 minutes to amplify samples in precycling, followed by 45 cycles of annealing at 62° C. for 5 seconds, annealing at 55.5° C. for 35 seconds, denaturing at 93° C. for 30 seconds.

Figure 5:
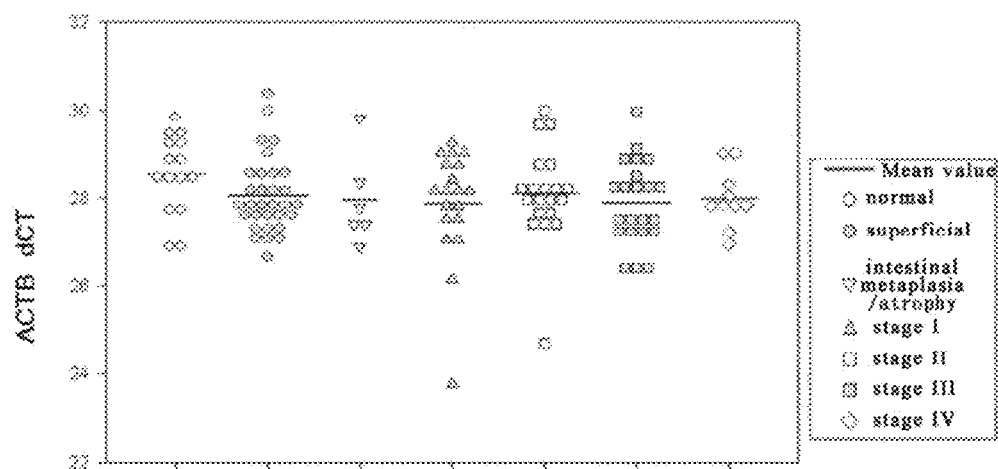
FIG. 5 shows the constant Ct values of β-actin in normal people, superficial, atrophic/intestinal metaplasia, gastric cancer stages I, II, III and IV.

Finally, the Ct values of the real-time PCR for Setptin9 gene in the genomic DNA samples of 15 normal people, 31 cases of superficial gastritis, 6 cases of atrophic gastritis/gastritis with intestinal metaplasia, 19 cases of gastric cancer stage I, 20 cases of gastric cancer stage II, 22 cases of gastric cancer stage III and 10 cases of gastric cancer stage IV were determined. The Ct values of the real-time PCR of β-actin in the genomic DNA samples of 15 normal people, 31 cases of superficial gastritis, 6 cases of atrophic gastritis/gastritis with intestinal metaplasia, 19 cases of gastric cancer stage I, 20 cases of gastric cancer stage II, 22 cases of gastric cancer stage III and 10 cases of gastric cancer stage IV were also determined, as shown in FIG. 5. It can be seen from FIG. 5 that the average Ct values of β-actin (ACTB) are very similar as the disease severity increases from normal people, superficial, atrophic gastritis/gastritis with intestinal metaplasia to gastric cancer stages I, II, III, and IV. Thus, the Ct values of β-actin are constant. The Ct of β-actin can serve as an internal reference for the PCR, i.e., an internal control.

Figure 6:
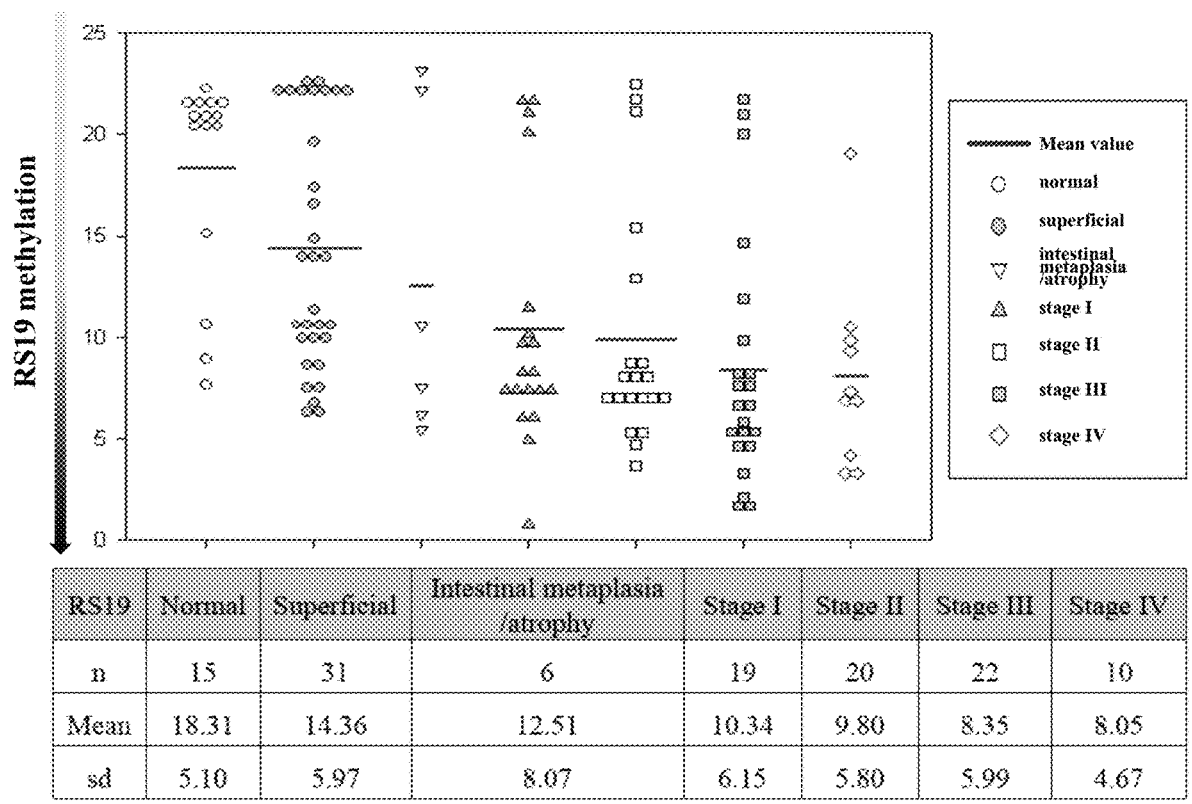
FIG. 6 shows the dCt values of RNF180 in normal people, superficial, atrophic/intestinal metaplasia, and gastric cancer stages I, II, III and IV.

The Ct values of the real-time PCR for RNF180 gene in the genomic DNA samples of 15 normal people, 31 cases of superficial gastritis, 6 cases of atrophic gastritis/gastritis with intestinal metaplasia, 19 cases of gastric cancer stage I, 20 cases of gastric cancer stage II, 22 cases of gastric cancer stage III and 10 cases of gastric cancer stage IV are determined, as shown in FIG. 6. The dCT value of RNF180 is obtained by subtracting the Ct of β-actin from the Ct of RNF180. In FIG. 6, the ordinate is the dCt or ΔCt value of RNF 180.

Similarly, the dCT value of Septin9 is obtained by subtracting the Ct of the actin from the Ct of Septin 9. The lower the dCt value is, the higher the methylation level is.

It can be seen from FIG. 6 that the dCt value of RNF180 is becoming lower and the methylation level is becoming higher as the disease severity increases from normal people, superficial gastritis, atrophic gastritis/gastritis with intestinal metaplasia to gastric cancer stages I, II, III and IV.

The above experimental results further demonstrat that the Ct or dCt value can be used to not only grade normal people, gastritis, and gastric cancers, but also further grade gastritis, for example, gastritis can be graded into mild gastritis (including superficial) and severe gastritis (including atrophic and with intestinal metaplasia). Furthermore, gastric cancer can be further graded based on the Ct or dCt value, for example, gastric cancer can be graded into gastric cancer stages I, II, III and IV.

Example 5: Dertermination of Positive Rates of Normal, Superficial Gastritis, Atrophic Gastritis/Gastritis with Intestinal Metaplasia, Gastric Cancer and Gastric Cancer Stages I, II, III and IV Based on Multiple Detection of Methylated DNA of Septin9 and RNF180 (RS19)

The samples were obtained from 15 normal people, 31 cases of superficial gastritis, 6 cases of atrophic gastritis/gastritis with intestinal metaplasia (including 3 cases of atrophic gastritis and 3 cases of gastritis with intestinal metaplasia), 74 cases of gastric cancer (including 19 cases of gastric cancer stage I, 20 cases of stage II, 22 cases of stage III and 10 cases of stage IV). The genomic DNA was extracted from each sample. The Extraction of the DNAs can be carried out with any standard means in the prior art, and particularly, in this example, the DNAs of all samples were extracted by the EPi proColon Plasma Quick Kit of Epigenomics AG.

The genomic DNA samples were then pretreated such that 5'-unmethylated cytosine base was converted to uracil, thymine, or another base which is different from cytosine in terms of hybridization behaviour. In the example, the pretreatment was achieved by treatment with a bisulfite reagent. The DNA modification with the bisulfite was carried out by the EPi proColon Plasma Quick Kit.

Next, the second set of primers and probes for RNF180 described above were added to the pre-treated genomic DNA samples of 15 normal people, 31 cases of superficial gastritis, 6 cases of atrophic gastritis/gastritis with intestinal metaplasia, 74 cases of gastric cancer (including 19 cases of stage I, 20 cases of stage II, 22 cases of stage III and 10 cases of stage IV) so as to carry out the PCR experiment for RNF 180, and the primers and probes for Septin9 and β-actin were added for multiple detection of the PCR experiments for RNF180, Septin9 and β-actin. The PCR reagents for Septin9 and β-actin were purchased from Epigenomics AG. The Real-time PCR was performed on the DNAs converted by bisulfite.

Wherein the PCR amplification conditions employed in the experiment were as follows: the real-time PCR detections were performed on a Life Technologies instrument (7500Fast). The PCR reaction mixture consisted of 35 ng DNA templates converted by bisulfite, 450 nM primers, 225 nM probes, 1UTaq polymerases, 200 um each dNTPs, 4.5 mM MgCl2 and 2×PCR buffer with a final volume of 30 ul, which was kept at 94° C. for 20 minutes to amplify samples in precycling, followed by 45 cycles of annealing at 62° C. for 5 seconds, annealing at 55.5° C. for 35 seconds, denaturing at 93° C. for 30 seconds.

Finally, the Ct values of real-time PCR for Setptin9 gene in the genomic DNA samples of 15 normal people, 31 cases of superficial gastritis, 6 cases of atrophic gastritis/gastritis with intestinal metaplasia, 74 cases of gastric cancer (including 19 cases of stage I, 20 cases of stage II, 22 cases of stage III and 10 cases of stage IV) were determined. The Ct values of real-time PCR for β-actin in the genomic DNA samples from 15 normal people, 31 cases of superficial gastritis, 6 cases of atrophic gastritis/gastritis with intestinal metaplasia, 74 cases of gastric cancer including 19 cases of stage I, 20 cases of stage II, 22 cases of stage III and 10 cases of stage IV were also determined. Further, the Ct values of real-time PCR for RNF180 gene in the genomic DNA samples of 15 normal people, 31 cases of superficial gastritis, 6 cases of atrophic gastritis/gastritis with intestinal metaplasia, 74 cases of gastric cancer (including 19 cases of stage I, 20 cases of stage II, 22 cases of stage III and 10 cases of stage IV) were determined. The Ct for β-actin served as an internal control. The dCT value of RNF180 was obtained by subtracting the Ct of β-actin from the Ct of RNF180. It was considered as positive for the diseases provided that dCt<10.

FIG. 7A shows the comparison of positive rates of RS19 between normal people, superficial gastritis, atrophic gastritis/gastritis intestinal metaplasia and gastric cancer. The ordinate represents positive rate, while the abscissa from left to right represents normal people, superficial gastritis, atrophic gastritis/gastritis with intestinal metaplasia and gastric cancer, respectively. It can be seen from FIG. 7A that the positive rate is becoming higher and higher as the disease severity increases from normal people, superficial gastritis, atrophic gastritis/gastritis with intestinal metaplasia to gastric cancer.

FIG. 7B shows the comparison of positive rate for RS19 between gastric cancer stages I, II, III and IV. The ordinate represents the positive rate, while the abscissa from left to right represents gastric cancer stages I, II, III and IV, respectively. It can be seen from FIG. 7B that the positive rate is becoming higher and higher as the disease severity increases from gastric cancer stages I, II, III to IV.

FIG. 7C shows the histogram of the average dCt values for RS19 of normal people, gastritis and gastric cancer, respectively. FIG. 7C further demonstrates the results of Example 2. In the detection of RNF180, there is a very significant difference of dCt value between gastric cancer and gastritis, a significant difference of dCt between normal people and gastritis, and an extremely significant difference of dCt between normal people and gastric cancer. Again, the results of the experiment confirm that the disease severity can be graded by the detection result of methylation of RNF180, for example, gastric cancer, gastritis, and normal people can be graded.

Furthermore, the methylation of RNF180 is of great significance in the chronic gastritis complicated with intestinal metaplasia. It is generally believed that chronic atrophic gastritis and chronic gastritis with intestinal metaplasia are more prone to canceration. In three samples which are diagnosed as chronic gastritis complicated with intestinal metaplasia according to pathological biopsies, the amounts of RNF180 in blood increase, the Ct values decrease significantly, with the average Ct of 7.9 and the positive rate of 100% (3/3). However, the positive rate of chronic atrophic gastritis is 33% (⅓), which is approximate to that of chronic superficial gastritis of 27%, see Table 4. It is estimated that the proportion of intestinal metaplasia in the patients who have common chronic superficial gastritis and are positive for RNF180 (27%), may increase if a biopsy is performed.

TABLE 4 dCT values of RNF180 in 3 cases of gastritis with intestinal metaplasia and 3 cases of chronic atrophic gastritis

| Gastritis | Case 1, complicated with intestinal metaplasia | Case 2, complicated with intestinal metaplasia | Case 3, complicated with intestinal metaplasia | Case 1, chronic atrophic gastritis | Case 2, chronic atrophic gastritis | Case 3, chronic atrophic gastritis |
| --- | --- | --- | --- | --- | --- | --- |
| dCT | 5.5 | 7.5 | 10.6 | 6.2 | 22.2 | 23.1 |

Therefore, RNF180 can also be used to distinguish gastritis with intestinal metaplasia from common gastritis without intestinal metaplasia, while the positive rate for RNF180 of gastritis with intestinal metaplasia is 100%, and the positive rate for RNF180 of common gastritis is about 27%.

Example 6: Improvement of Combination of Septin9 and RNF180 on Specificity and Sensitivity of Gastric Cancer Detection The samples were obtained from 15 normal people, 37 patients with gastritis and 74 patients with gastric cancer. The Genomic DNA was extracted from each sample. The extraction of DNA can be carried out using any standard means in the prior art, and in particular, in this example, the DNAs of all samples were extracted by the EPi proColon Plasma Quick Kit of Epigenomics AG.

The genomic DNA samples were then pretreated such that 5'-unmethylated cytosine base was converted to uracil, thymine, or another base which is different from cytosine in terms of hybridization behaviour. In the example, this pretreatment was achieved by treatment with a bisulfite reagent. The DNA modification with bisulfite was carried out by the EPi proColon Plasma Quick Kit.

Next, the second set of primers and probes for RNF180 described above were added to the pre-treated genomic DNA samples to carry out the PCR experiment for RNF 180, and the primers and probes for Septin9 and β-actin were added for multiple detection of the PCR experiments for RNF180, Septin9 PCR, and β-actin. The PCR reagents for Septin9 and β-actin were purchased from Epigenomics AG. The Real-time PCR was performed with the bisulfite-converted DNA.

The PCR amplification conditions employed in the experiment were as follows: the real-time PCR detection was performed on a Life Technologies instrument (7500Fast). The PCR reaction mixture consisted of the bisulfite-converted DNA templates 35 ng and 450 nM primers, 225 nM probes, 1UTaq polymerases, 200 um each dNTPs, 4.5 mM MgCl2 and 2×PCR buffer with a final volume of 30 ul, which was kept at 94° C. for 20 minutes to amplify samples in precycling, followed by 45 cycles of annealing at 62° C. for 5 seconds, annealing at 55.5° C. for 35 seconds, denaturing at 93° C. for 30 seconds.

Finally, the Ct values of real-time PCR for Setptin9 gene in the genomic DNA samples of 15 normal people, 37 patients with gastritis, and 74 patients with gastric cancer were determined. And the Ct values of real-time PCR for β-actin in the above-described DNA samples were determined. And the Ct values of real-time PCR for RNF180 gene in the above-described DNA samples were determined. The Ct of actin served as an internal control. The dCT value of RNF180 was obtained by subtracting the Ct of β-actin from the Ct of RNF180, and the dCT value of Setptin9 was obtained by subtracting the Ct of β-actin from the Ct of Setptin9.

Figure 8A:
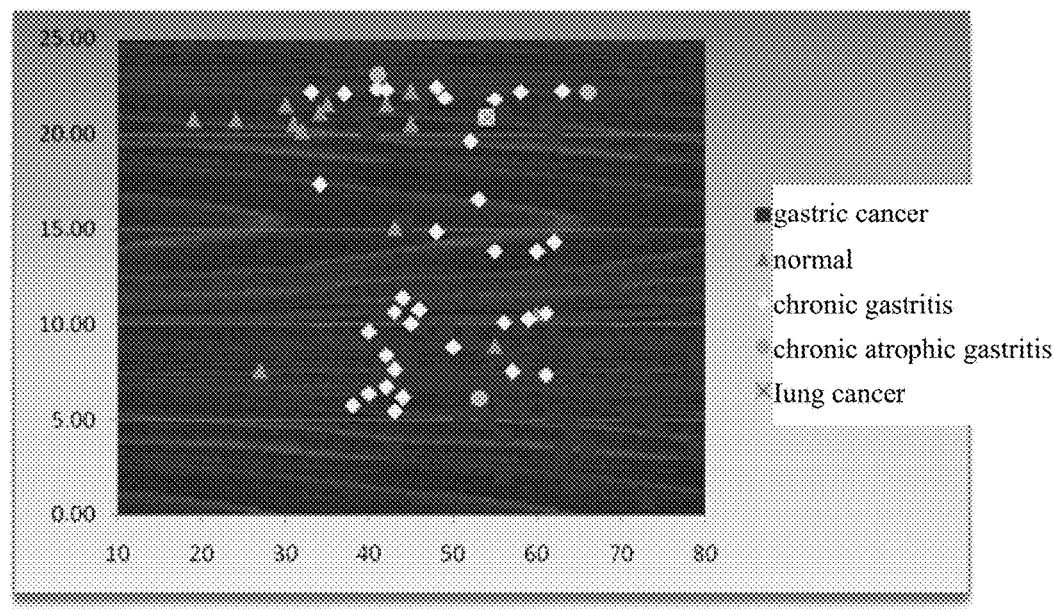
FIG. 8A shows a graph of the relation between the methylation level of RNF180 and age.

The content of the methylated RNF180 gene in peripheral blood tends to increase as age increases, and FIG. 8A is plotted with age as the abscissa and the dCT value of RNF180 as the ordinate. Since the elderly has a certain degree of gastritis more or less, it is difficult to distinguish whether age factor or gastritis factor leads to the elevated content of the methylated RNF180 gene in the peripheral blood, which has a significant impact on the specificity and reliability of the detection of gastritis and gastric cancer. As shown in FIG. 8A, in the elderly stage, chronic gastritis (rhomboid) and gastric cancer (square) are partially intersected, thus affect the detection of gastric cancer.

Figure 8B:
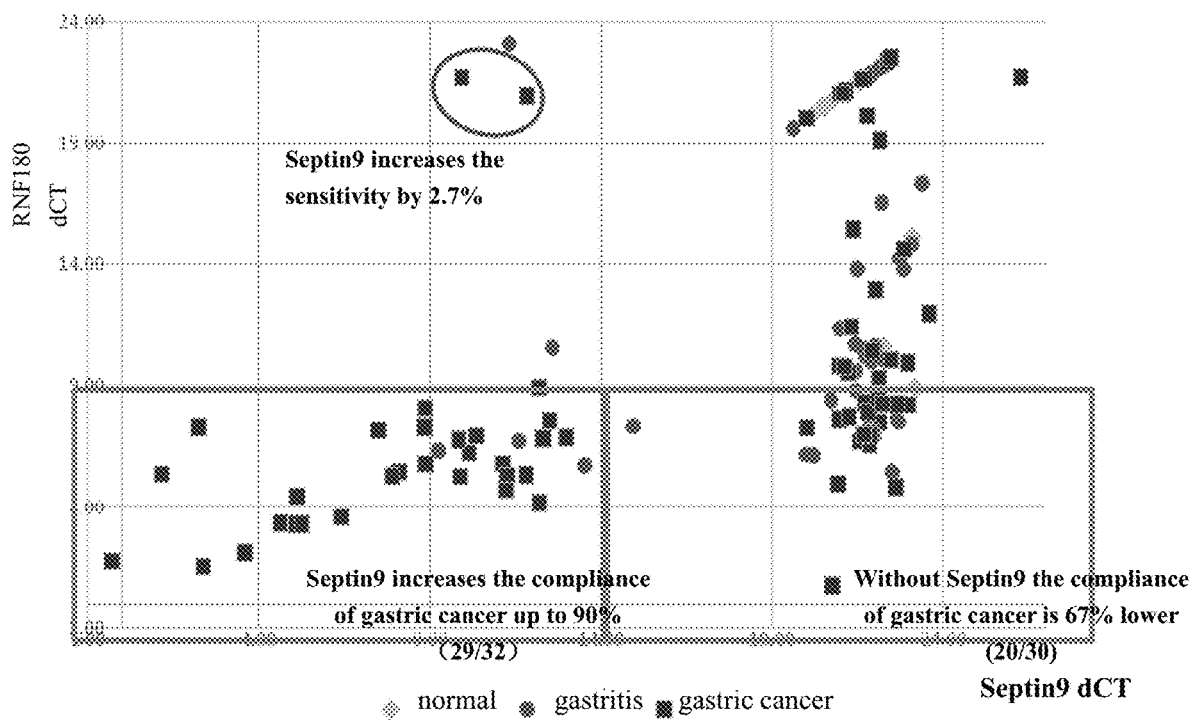
FIG. 8B is a schematic diagram showing that the combination of Septin9 and RNF180 improves the specificity and sensitivity of detection for gastric cancer.

FIG. 8B is plotted with the dCT value of Setptin9 as the abscissa and the dCT value of RNF180 as the ordinate. As shown in FIG. 8B, when the critical value of dCT for Septin9 is selected to be 14 and the critical value of dCT for RNF180 is selected to be 10, the points in the left panel indicate that the detection result of Septin9 is positive, and the detection result of RNF180 is also positive. While the right panel indicates that the detection result of Septin9 is negative, and the detection result of RNF180 is positive. For this example, Septin9 and RNF180 are selected to be simultaneously positive, which increase the specificity for a portion of gastric cancers, wherein approximately 39% (29/74) of gastric cancers achieve a compliance of 90% (29/32), so as to effectively exclude the negative effects of gastritis and age on RNF180. Therefore, the combination of the two biomarkers Septin9 and RNF180 can reduce the negative effects of high non-specificity (age, gastritis) of RNF180 on the diagnosis of gastric cancer, improve the specificity of gastric cancer detection and increase the sensitivity of gastric cancer detection.

In terms of the sensitivity, two cases of gastric cancer are negative for RNF180, but positive for Septin9, and Septin9 can increase the sensitivity by 2.7% (2/74). So if the two biomarkers Septin9 and RNF180 are combined together to perform the detection, the specificity and sensitivity of gastric cancer detection can be improved.

In summary, the content of the methylated RNF180 gene in peripheral blood tends to increase as age increases, but since the elderly has a certain degree of gastritis more or less, it is difficult to distinguish whether age factor or gastritis factor leads to the elevated content of the methylated RNF180 gene in the peripheral blood, which has a significant impact on the specificity and reliability of the detection of gastritis and gastric cancer. As the effects of the factors, such as age and chronic gastritis on Septin9 gene can be ignored, Septin9 can be used to confirm the detection of gastric cancer by RNF180.

Example 7: Sensitivity and Specificity of Multiple Detection of Methylated DNA of Septin9 and RNF180 (RS19) in Normal People and Gastric Cancer The samples were obtained from 15 normal people and 74 patients with gastric cancer. The genomic DNA was extracted from each sample. The extraction of DNA can be carried out using any standard means in the prior art, and in particular, in this example, the DNAs of all samples were extracted by the EPi proColon Plasma Quick Kit of Epigenomics AG.

The genomic DNA sample was then pretreated such that 5'-unmethylated cytosine base was converted to uracil, thymine, or another base which is different from cytosine in terms of hybridization behaviour. In the example, this pretreatment was achieved by treatment with a bisulfite reagent. The DNA modification with bisulfite was carried out by the EPi proColon Plasma Quick Kit.

Next, the second set of primers and probes for RNF180 described above were added to the pre-treated genomic DNA samples of 15 normal people and 74 patients with gastric cancer to carry out the PCR experiment for RNF 180, and the primers and probes for Septin9 and β-actin were added for multiple detection of the PCR experiments for RNF180, Septin9 and β-actin. The PCR reagents for Septin9 and β-actin were purchased from Epigenomics AG. The Real-time PCR was performed with the bisulfite-converted DNAs.

The PCR amplification conditions employed in the experiment were as follows: the real-time PCR detection was performed on a Life Technologies instrument (7500Fast). The PCR reaction mixture consisted of the bisulfite-converted DNA templates 35 ng and 450 nM primers, 225 nM probes, 1UTaq polymerases, 200 um each dNTPs, 4.5 mM MgCl2 and 2×PCR buffer with a final volume of 30 ul, which was kept at 94° C. for 20 minutes to amplify the samples in precycling, followed by 45 cycles of annealing at 62° C. for 5 seconds, annealing at 55.5° C. for 35 seconds, denaturing at 93° C. for 30 seconds.

Figure 9:
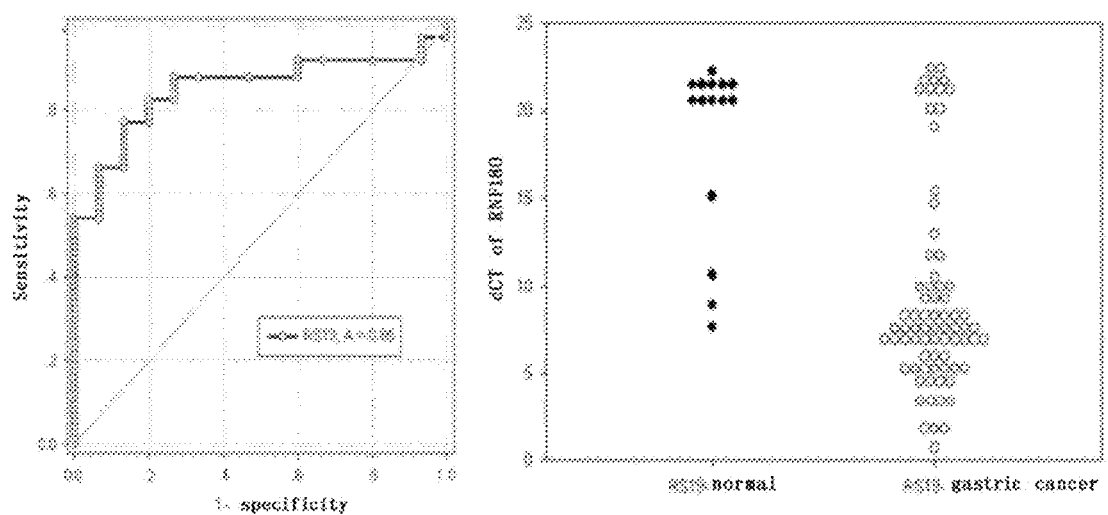
FIG. 9 shows the sensitivity and specificity of multiple detection (RS19) of normal and gastric cancer based on the methylated DNAs of Septin9 and RNF180.

Finally, the Ct values of real-time PCR for Setptin9 gene in the genomic DNA samples of 15 normal people and 74 patients with gastric cancer were determined. And the Ct values of real-time PCR for β-actin in the genomic DNA samples of 15 normal people and 74 patients with gastric cancer were determined. And the Ct values of real-m time PCR of RNF180 gene in the genomic DNA samples from 15 normal people and 74 patients with gastric cancer were determined. The Ct of actin served as an internal control. The dCT value of RNF180 was obtained by subtracting the Ct of β-actin from the Ct of RNF180, as shown in FIG. 9. FIG. 9 also shows the sensitivity and specificity of the detection of gastric cancer when the critical values are 10 and 15, respectively, as well as the ROC curve.

Therefore, as shown in the table of FIG. 9, when the dCut value is selected to be 10, the sensitivity is 74% and the specificity is 87%, and when the dCut value is selected to be 15, the sensitivity is 84% and the specificity is 73%. Thus, the dCut value or Cut value can vary according to the selected sensitivity and specificity. Considering the actual demand of sensitivity and specificity, the dCut value is preferably selected to be 10.

Example 8: Sensitivity and Specificity of Multiple Detection of Methylated DNA of Septin9 and RNF180 (RS19) in Normal and Gastritis (Chronic, Superficial, Ulcerative)

The samples were obtained from 15 normal people and 33 patients with gastritis (chronic, superficial, ulcerative). The Genomic DNA was extracted from each sample. The extraction of DNA can be carried out using any standard means in the prior art, and in particular, in this example, the DNAs of all samples were extracted by the EPi proColon Plasma Quick Kit of Epigenomics AG.

The genomic DNA samples were then pretreated such that 5'-unmethylated cytosine base was converted to uracil, thymine, or another base which is different from cytosine in terms of hybridization behaviour. In the example, this pretreatment was achieved by treatment with a bisulfite reagent. The DNA modification with bisulfite was carried out by the EPi proColon Plasma Quick Kit.

Next, the second set of primers and probes for RNF180 described above were added to the pre-treated genomic DNA samples from 15 normal people and 33 patients with gastritis (chronic, superficial, ulcerative) to carry out the PCR experiment for RNF 180, and the primers and probes for Septin9 and β-actin were added for multiple detection of PCR experiments for RNF180, Septin9 and β-actin. The PCR reagents for Septin9 and β-actin were purchased from Epigenomics AG. The Real-time PCR was performed with the bisulfite-converted DNAs.

The PCR amplification conditions employed in the experiment were as follows: the real-time PCR detection was performed on a Life Technologies instrument (7500Fast). The PCR reaction mixture consisted of the bisulfite-converted DNA templates 35 ng and 450 nM primers, 225 nM probes, 1UTaq polymerases, 200 um each dNTPs, 4.5 mM MgCl2 and 2×PCR buffer with a final volume of 30 ul, which was kept at 94° C. for 20 minutes to amplify the samples in precycling, followed by 45 cycles of annealing at 62° C. for 5 seconds, annealing at 55.5° C. for 35 seconds, denaturing at 93° C. for 30 seconds.

Figure 10:
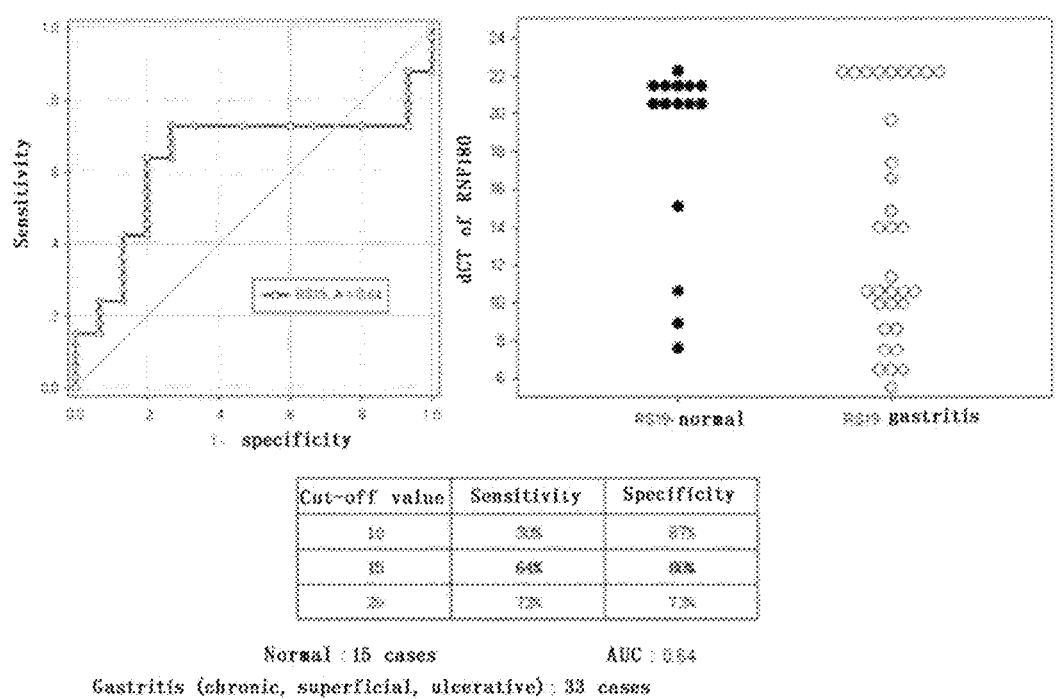
FIG. 10 shows the sensitivity and specificity of multiple detection (RS19) of normal and gastritis (chronic, superficial and ulcerative) based on the methylated DNAs of Septin9 and RNF180.

Finally, the Ct values of real-time PCR for Setptin9 gene in the genomic DNA samples of 15 normal people and 33 patients with gastritis (chronic, superficial, ulcerative) were determined. And the Ct values of real-time PCR of β-actin in the genomic DNA samples of 15 normal people and 33 patients with gastritis (chronic, superficial, ulcerative) were determined. And the Ct values of real-time PCR of RNF180 gene in the genomic DNA samples of 15 normal people and 33 patients with gastritis (chronic, superficial, ulcerative) were determined. The Ct of β-actin served as an internal control. The dCT value of RNF180 was obtained by subtracting the Ct of β-actin from the Ct of RNF180, as shown in FIG. 10. FIG. 10 also shows the sensitivity and specificity of the detection of gastritis (chronic, superficial, ulcerative) when the critical values are 10, 15 and 20, respectively, as well as the ROC curve.

Therefore, as shown in the table of FIG. 10, when the dCut value is selected to be 10, the sensitivity is 30% and the specificity is 87%, when the dCut value is selected to be 15, the sensitivity is 64% and the specificity is 80%, and when the dCut value is selected to be 20, the sensitivity is 73% and the specificity is 73%. Thus, the dCut value or Cut value can vary according to the selected sensitivity and specificity. Considering the actual demand for sensitivity and specificity, the dCut value is preferably selected to be 15.

Example 9: Sensitivity and Specificity of Multiple (RS19) Detection of Normal and Gastritis (all) Based on Methylated DNA of Septin9 and RNF180

The samples were obtained from 15 normal people and 37 patients with gastritis (all). The genomic DNA was extracted from each sample. The extraction of DNA can be carried out with any standard means in the prior art, and particularly, in this example, the DNAs of all samples were extracted by the EPi proColon Plasma Quick Kit of Epigenomics AG.

The genomic DNA sample was then pretreated such that the 5'-unmethylated cytosine base was converted to uracil, thymine, or another base which is different from cytosine in terms of hybridization behaviour. In the example, the pretreatment was achieved by treatment with a bisulfite reagent. The DNA modification with the bisulfite was carried out by the EPi proColon Plasma Quick Kit.

Next, the second set of primers and probes for RNF180 described above were added to the above pre-treated genomic DNA samples of 15 normal people and 37 patients with gastritis (all) to carry out the PCR experiment for RNF 180, and the primers and probes for Septin9 and β-actin were added for the PCR experiment for multiple detection of the PCR experiments for RNF180, Septin9 and β-actin. The PCR reagents for Septin9 and β-actin were purchased from Epigenomics AG. The Real-time PCR was performed on the DNAs converted by a bisulfite.

Wherein, the PCR amplification conditions employed in the experimental example were as follows: the real-time PCR was performed on a Life Technologies instrument (7500Fast). The mixture for PCR reaction consisted of 35 ng DNA templates converted by bisulfite and 450 nM primers, 225 nM probes, 1UTaq polymerases, 200 um each dNTPs, 4.5 mM MgCl2 and 2×PCR buffer with a final volume of 30 ul, which was kept at 94° C. for 20 minutes to amplify samples in precycling, followed by 45 cycles of annealing at 62° C. for 5 seconds, annealing at 55.5° C. for 35 seconds, denaturing at 93° C. for 30 seconds.

Figure 11:
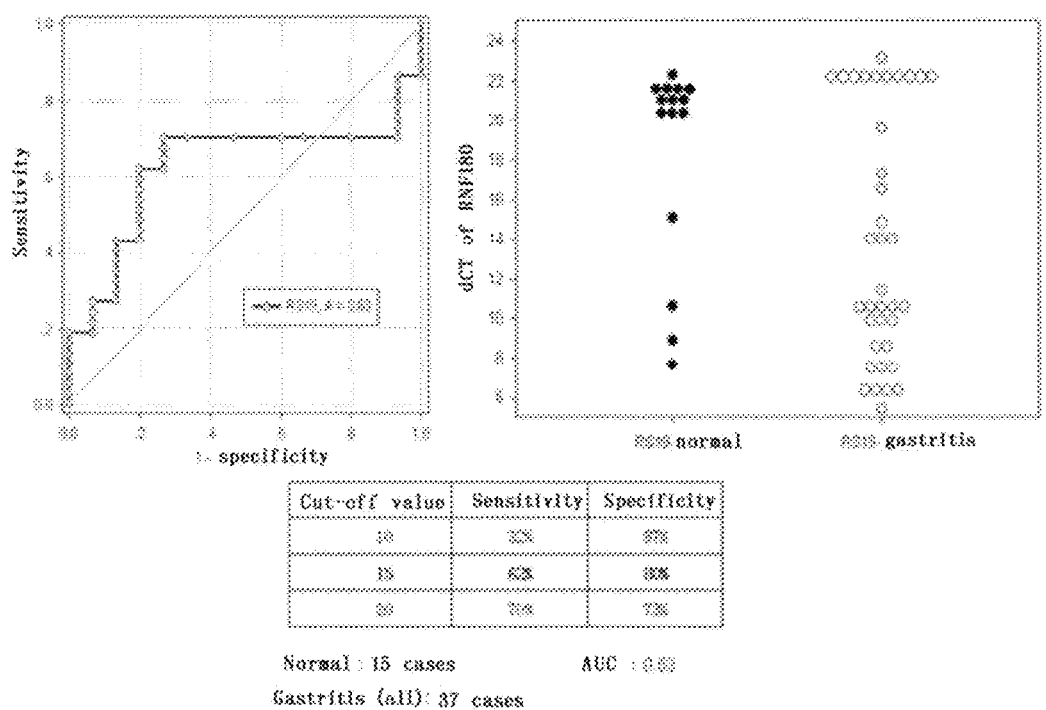
FIG. 11 shows the sensitivity and specificity of multiple detection (RS19) of normal and gastritis (all) based on the methylated DNAs of Septin9 and RNF180.

Finally, the Ct values of real-time PCR for Setptin9 gene in the genomic DNA samples of 15 normal people and 37 patients with gastritis (all) were determined, and the Ct values of real-time PCR of β-actin in the genomic DNA samples of 15 normal people and 37 patients with gastritis (all) were determined. The Ct values of real-time PCR of RNF180 gene in the genomic DNA samples of 15 normal people and 37 patients with gastritis (all) were also determined. The Ct value of β-actin served as internal controls. The dCT value of RNF180 was obtained by subtracting the Ct of β-actin from the Ct of RNF180, as shown in FIG. 11. FIG. 11 also shows the sensitivity and specificity of the detection of gastritis (all) when the threshold values are 10, 15 and 20, respectively, as well as the ROC curve.

Therefore, as shown in the table of FIG. 11, when the dCut value is selected to be 10, the sensitivity is 32% and the specificity is 87%; when the dCut value is selected to be 15, the sensitivity is 62% and the specificity is 80%; and when the dCut value is selected to be 20, the sensitivity is 70% and the specificity is 73%. Thus, the dCut value or Cut value can vary according to the selected sensitivity and specificity. Combining the actual demand for sensitivity and specificity, the dCut value is preferably selected to be 15.

In conclusion, in the present application, it is found through the experiments that there is a great difference of methylation level of RNF180 gene between gastritis and gastric cancer. The amount of RNF180 increases gradually from normal group, chronic superficial gastritis (including general chronic gastritis and ulcerative gastritis) group, chronic atrophic gastritis (including chronic gastritis complicated with intestinal metaplasia) group to gastric cancer stages I to IV group, while the Ct value decreases gradually. The positive rate also gradually increases from normal group to the gastric cancer group in the same order. Therefore, the present application provides a method for grading gastric cancer and gastritis by measuring the methylation level of RNF180 gene in a sample, thereby provides a noninvasive and rapid method for screening gastric cancer and gastritis.

Furthermore, the amount of methylated RNF180 gene in peripheral blood tends to increase as age increases. However, since the elderly has a certain degree of gastritis more or less, it is difficult to distinguish whether age factor or gastritis factor leads to the elevated amount of methylated RNF180 gene in the peripheral blood, which has a significant impact on the specificity and reliability of the detection of gastritis and gastric cancer. Therefore, taken it into consideration, Septin9 is simultaneously introduced in the detection. As the impact of age and gastritis on Septin9 gene can be ignored, Septin9 can be used to confirm the detection of gastric cancer. Specifically, about 40% of gastric cancers are positive for both Septin9 and RNF180, and the double positives can be used as a criterion to achieve specificity up to 90%. Also, according to certain specific embodiments, some gastric cancers are negative for RNF180, but positive for Septin9, and these gastric cancers can be detected by Septin9 with the sensitivity increased by about 3%. Therefore, both the sensitivity and specificity can be improved by combining the two biomarkers, Septin9 and RNF180 for grading gastritis and gastric cancer.

Finally, a simultaneous bi-channel detection of the two biomarkers, Septin9 and RNF180, can be conveniently achieved by a real-time PCR assay of the DNA in plasma sample, and whether the sample is positive can be quickly and easily determined according to the real-time PCR cycle threshold (Ct) value. Thus, a noninvasive and rapid method for grading cancer and inflammation is provided.

All the publications and patent applications mentioned in the specification indicate the technical level of those skilled in the field to which the invention is relevant. All the publications and patent applications are incorporated herein by reference, as if each of them is specifically and individually indicated to be incorporated herein by reference. The mere reference to these publications and patent applications is not to be construed as an admission that they are the prior arts to the present application.

While various aspects and embodiments of the present invention are disclosed herein, other aspects and embodiments will be apparent to those skilled in the art. The various aspects and embodiments disclosed herein are only for illustrative purposes and are not intended to be limiting. The scope and spirit of the present invention are to be determined only by the appended claims.

Unless otherwise expressly stated, the terms and phrases used herein and variations thereof should be construed as open-ended, not limited. In some instances, the appearance of extensible terms and phrases such as "one or more", "at least", "but not limited to" or the like should not to be construed as intention or requirement to indicate a narrower condition in an example that may be without such extensible terms.

The invention claimed is:

1. A method for detecting gastric cancer in an individual, comprising:
   detecting the methylation level of at least one CpG dinucleotide of the DNA sequence of RNF180 gene or a fragment thereof in a biological sample isolated from the individual by using a combination of primers and probes comprising SEQ ID NOs: 4, 7, and 8; SEQ ID NO: 7 being the probe and being fluorescently labeled, wherein the methylation level of the at least one CpG dinucleotide of RNF180 gene or fragment thereof is determined by a cycle threshold Ct value of polymerase chain reaction;
   detecting the methylation level of at least one CpG dinucleotide of the DNA sequence of Septin9 gene or a fragment thereof in the biological sample, by using a combination of primers and a probe of SEQ ID NOs: 14-16, SEQ ID NO: 16 being the probe, wherein the methylation level of the at least one CpG dinucleotide of the DNA sequence of Septin9 gene or fragment thereof is determined by a cycle threshold Ct value of polymerase chain reaction; and determining the presence of gastric cancer in the individual by combining the detection results of methylation of RNF180 gene or fragment thereof and the detection result of methylation of Septin9 gene or fragment thereof.

2. The method according to claim 1, further comprising: treating Septin9 gene or fragment thereof and RNF180 gene or fragment thereof with a reagent that converts 5-unmethylated cytosine base of a gene to uracil or other base that is detectably different from cytosine in terms of hybridization performance;
   contacting Septin9 gene or fragment thereof and RNF180 gene or fragment thereof treated by the reagent with an amplification enzyme and respective primers from the combinations of primers and probes such that the treated genes or fragments thereof are amplified to produce amplification products or are not amplified;
   detecting the amplification products with the respective probes from the combinations of primers and probes; and
   determining the methylation level of at least one CpG dinucleotide of the DNA sequences of Septin9 and the methylation level of at least one CpG dinucleotide of the DNA sequence of RNF180 gene or fragment thereof based on the presence or absence of the amplification products.

3. The method according to claim 1, wherein the biological sample of the individual is selected from the group consisting of cell lines, histological sections, tissue biopsies, paraffin-embedded tissues, body fluids, stool, colonic effluent, urine, plasma, serum, whole blood, isolated blood cells, cells isolated from blood, and a combination thereof.

4. The method according to claim 3, wherein the biological sample of the individual is plasma.

* * * * *

```
                        SEQUENCE LISTING

<160> NUMBER OF SEQ ID NOS: 16

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
gttcgaggtc gcggggtc                                                 18

<210> SEQ ID NO 2
<211> LENGTH: 26
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(1)
<223> OTHER INFORMATION: link CAL Fluor Red
<220> FEATURE:
<221> NAME/KEY: misc_feature
<222> LOCATION: (26)..(26)
<223> OTHER INFORMATION: link BHQ2

<400> SEQUENCE: 2
aacgctcgaa ctatacctac aacccc                                        26

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
acaaaaacca aaccccgcg                                                19

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
gcggggtttg gtttttgt                                                 18

<210> SEQ ID NO 5
<211> LENGTH: 18
<212> TYPE: DNA
<213> ORGANISM: Artificial Sequence
<220> FEATURE:
<223> OTHER INFORMATION: probe
```

<220> FEATURE:
<221> NAME/KEY: misc_feature
<222> LOCATION: (1)..(1)
<223> OTHER INFORMATION: link CAL Fluor Red
<220> FEATURE:
<221> NAME/KEY: misc_feature
<222> LOCATION: (18)..(18)
<223> OTHER INFORMATION: link BHQ2

<400> SEQUENCE: 5
ccgacgacga cgataccg                                                   18

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
acaaccaaac tctaaaaact cg                                              22

<210> SEQ ID NO 7
<211> LENGTH: 21
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(1)
<223> OTHER INFORMATION: link CAL Fluor Red
<220> FEATURE:
<221> NAME/KEY: misc_feature
<222> LOCATION: (21)..(21)
<223> OTHER INFORMATION: link BHQ2

<400> SEQUENCE: 7
cgtcggagtc gtagcgagtt t                                               21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
aaaacctcca acttcacacc c                                               21

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
cgccaacaac caaactctaa                                                 20

<210> SEQ ID NO 10
<211> LENGTH: 606
<212> TYPE: DNA
<213> ORGANISM: Artificial Sequence
<220> FEATURE:
<223> OTHER INFORMATION: promoter region of RNF180 (-234bp to +372bp of
      the transcription initiation site)

<400> SEQUENCE: 10

```
gataatttct gtggctctgg taagggatg acaagggaga aaaactttcc cacggttccg    60
tctggcccgc ggcgcttgtc tgcctgcgcg gggtcaaagc ccggcgccgc ccacgcgcgg   120
ctcgggtggg aacccgcaga cgtggggcga gcagggccgc tggctgtggc gggcgagcgc   180
cggggcgcca cgtccgaggc cgcggggtcg gggctgcagg cacagctcga gcgctttccg   240
cggggtttgg ctcctgtcgc ttcccgtctc gccgaaccgg catcgccgcc gccggagccg   300
cagcgagtcc tcagagcctg gctgctggcg gccgggagcg ccgggacggg gcgcgaagcc   360
ggaggctccg ggacgtggat acaggtaaag gccggcgggt cggagtcggg cggggcgcgg   420
cggcggcgcc tctcggaggg acctggcctc ggccgggccc tacccagccg cggtggcccg   480
ggcccccacg ttggcccagg cggggacgtg ccaaggggct gggctagggt tgccgctggc   540
ctggccgcct ctcgcccggc gggcctcagg tgacgcggcc gcggcttaac tttcgcacct   600
gaggct                                                             606

<210> SEQ ID NO 11
<211> LENGTH: 302
<212> TYPE: DNA
<213> ORGANISM: Artificial Sequence
<220> FEATURE:
<223> OTHER INFORMATION: promoter region of RNF180 (-167bp to +135bp of
      the transcription initiation site)

<400> SEQUENCE: 11
cgcggcgctt gtctgcctgc gcggggtcaa agcccggcgc cgcccacgcg cggctcgggt    60
gggaacccgc agacgtgggg cgagcagggc cgctggctgt ggcgggcgag cgccggggcg   120
ccacgtccga ggccgcgggg tcgggctgc aggcacagct cgagcgcttt ccgcggggtt   180
tggctcctgt cgcttcccgt ctcgccgaac cggcatcgcc gccgccggag ccgcagcgag   240
tcctcagagc ctggctgctg gcggccggga gcgccgggac ggggcgcgaa gccggaggct   300
cc                                                                 302

<210> SEQ ID NO 12
<211> LENGTH: 178
<212> TYPE: DNA
<213> ORGANISM: Artificial Sequence
<220> FEATURE:
<223> OTHER INFORMATION: promoter region of RNF180 (-43bp to +135bp of
      the transcription initiation site)

<400> SEQUENCE: 12
gtccgaggcc gcggggtcgg ggctgcaggc acagctcgag cgctttccgc ggggtttggc    60
tcctgtcgct tcccgtctcg ccgaaccggc atcgccgccg ccggagccgc agcgagtcct   120
cagagcctgg ctgctggcgg ccgggagcgc cgggacgggg cgcgaagccg gaggctcc     178

<210> SEQ ID NO 13
<211> LENGTH: 1405
<212> TYPE: DNA
<213> ORGANISM: Artificial Sequence
<220> FEATURE:
<223> OTHER INFORMATION: promoter sequence of Septin9

<400> SEQUENCE: 13
cgttacccga gttgtaaagg gcggctccct gtgtctgccc cgctgcaccg atacaccgag    60
ctgcgcacgg tgcccagcgc agggagaaca aatgatcatc tgtccaacgc gcccatttac   120
aggtgaggaa actaaggctc caactcaatc gacgcactct gccctttga ttaccagaaa   180
```

-continued

| | |
|---|---|
| agtagcagga caggtgtcct gtcccgccct accccggccc actaagccgg caccccggct | 240 |
| ccgaccccg gctgtgcccg gcgccgccgc ggtgcccggc gccgccgcct cgcccggcgg | 300 |
| ggccgcccgg agcgcccgca cctccgcccg cttccacctg gccgggcccg cccgcccgg | 360 |
| actcgggact gggaagtgcg gcgactcccg gaaccagcca ttggcgccag cgcggggagc | 420 |
| tgggggtgca gagctgcggg cgcggcgggc cacgcaggcg gcccccaccc ccggcctggc | 480 |
| ctggtctggt ctggtctgcg ctgccgcgcg ggggcgcccc ctcccaggcc cggcgcccgc | 540 |
| cagccccgct ccgccaggtg cagcgcagcg caggggtggg cggggtggg gctcggcgcg | 600 |
| cacgttcacg gggcggggag ggggcgggtc agggcggga ccacagccgg ctgggccggg | 660 |
| gttctatgcg catctccggg gaggggcggg gcggggcgg ggccggggcg gggcccggtc | 720 |
| ggtgcactcc agacggcggg ccgcccctc ttcccgcctt cctactaccg gcccaggatt | 780 |
| agcgccctgg gagcgcgcgc cccgctgcct cgccgccaca ctttcctggg agcggcggcc | 840 |
| acggaggcac catgaagaag tcttactcag gtgggcttcg cgcccggggt ggggaggggt | 900 |
| cggtgtcccg ggaccagcgc tgctcacctg agtgcctgcg gccgggagtg gcgaggcgcc | 960 |
| cccggagctg agcgagtccc cgcggcgggc acactgcagg tcgagttcct cccaggacag | 1020 |
| ggccgctgtc gggccgcttt cgacctgagc cgaccgtccc ctgcgctgtc tccagccctt | 1080 |
| gctcgagtgt cggaggggct gccctggggg acgctccctc ttcctcgccc cttgcaccct | 1140 |
| cgcaggaatc gctgactttc caggtcggcc gggtgctttg ggtccctgtg cgtctgtgtg | 1200 |
| ggtgaatggg gtcggggcta ggtggagggg tgtccttggg ttcagcctct agggctggtg | 1260 |
| gtccaggccg cagcatcctt tcttcggatt ctcttcggtt tctcctctac ttagtggggc | 1320 |
| acgggacggc ctccagatgg gaccgtccag cagcgcccaa acttggcgac tcgggttcac | 1380 |
| gttttgcgct caggacgccg cccgc | 1405 |

<210> SEQ ID NO 14
<211> LENGTH: 26
<212> TYPE: DNA
<213> ORGANISM: Artificial Sequence
<220> FEATURE:
<223> OTHER INFORMATION: primer

<400> SEQUENCE: 14
gtagtagtta gtttagtatt tatttt                                        26

<210> SEQ ID NO 15
<211> LENGTH: 17
<212> TYPE: DNA
<213> ORGANISM: Artificial Sequence
<220> FEATURE:
<223> OTHER INFORMATION: primer

<400> SEQUENCE: 15
cccaccaacc atcatat                                                  17

<210> SEQ ID NO 16
<211> LENGTH: 19
<212> TYPE: DNA
<213> ORGANISM: Artificial Sequence
<220> FEATURE:
<223> OTHER INFORMATION: probe

<400> SEQUENCE: 16 gaacccccgcg atcaacgcg                                               19